United States Patent [19]
Zucker et al.

[11] Patent Number: 5,603,328
[45] Date of Patent: Feb. 18, 1997

[54] INFRA-RED VASCULAR ANGIOGRAPHY SYSTEM

[75] Inventors: Menachem S. Zucker, Kiryat Motzkin; Gabriel J. Iddan, Haifa, both of Israel

[73] Assignee: The State of Israel, Ministry of Defence, Armament Development Authority, Tel-Aviv, Israel

[21] Appl. No.: 183,072

[22] Filed: Jan. 18, 1994

[30]    Foreign Application Priority Data

Jan. 18, 1993   [IL]   Israel ........................................ 104423

[51] Int. Cl.$^6$ ...................................................... A61B 6/00
[52] U.S. Cl. ........................ 128/664; 128/665; 250/330
[58] Field of Search ...................................... 128/664, 665, 128/654, 653.1; 250/346, 347, 330–332; 600/109, 112, 113, 103, 160, 131, 163, 167, 176

[56]                 References Cited

U.S. PATENT DOCUMENTS

| | | | |
|---|---|---|---|
| 4,711,999 | 12/1987 | Shishido et al. | 600/167 |
| 4,846,155 | 7/1989 | Kimura | 600/167 |
| 4,868,644 | 9/1989 | Yabe et al. | 600/131 |
| 4,947,245 | 8/1990 | Ogawa et al. | 600/167 |
| 4,953,539 | 9/1990 | Nakamura et al. | 600/109 |
| 4,967,276 | 10/1990 | Murakami et al. | |
| 4,987,305 | 1/1991 | Bornstein et al. | 250/352 |
| 4,995,398 | 2/1991 | Turnidge | |
| 5,222,477 | 6/1993 | Lia | 600/167 |
| 5,351,677 | 10/1994 | Kami et al. | 600/167 |
| 5,417,210 | 5/1995 | Funda et al. | 600/109 |

FOREIGN PATENT DOCUMENTS 008272   11/1988   WIPO ..................................... 128/604

OTHER PUBLICATIONS

Mohr et al., "Thermal Coronary Angiography: A Method for Assessing Graft Patency and Coronary Anatomy in Coronary By–Pass Surgery", *The Annals of Thoracic Surgery*, 1989, pp. 47, 441–449.

*Primary Examiner*—Marvin M. Lateef
*Assistant Examiner*—Brian L. Casler
*Attorney, Agent, or Firm*—Cowan, Liebowitz & Latman, P.C.

[57]                 ABSTRACT

An infra-red vascular angiography system comprising a readily displaceable infra-red camera including an infra-red optical assembly of high sensitivity capable of receiving and transmitting with minimal distortion an infra-red image of an object within an angular range of substantially ±45° with respect to a normal to the object; infrared detector for detecting, the infra-red image transmitted from the optical assembly and converting it into successive electric output signals; video imaging device coupled to the detector for digitizing the output signals and converting them into successive digitized video image frames or successive portions of them; image processor coupled to the imaging device adapted to receive the successive video frames or portions of them so as to process them so as to form enhanced video images and display device coupled to the image processor. The system is furthermore provided with visible range optical assemblies and detector and switching device coupled to the image processor, the latter being adapted to route either or both infra-red and visible range sets of enhanced video images to a display device.

53 Claims, 12 Drawing Sheets

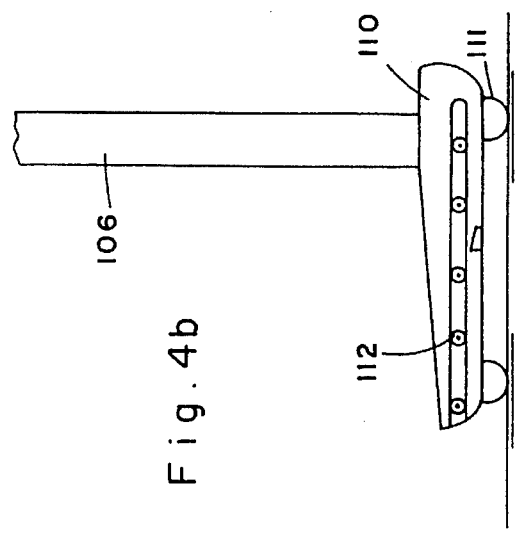
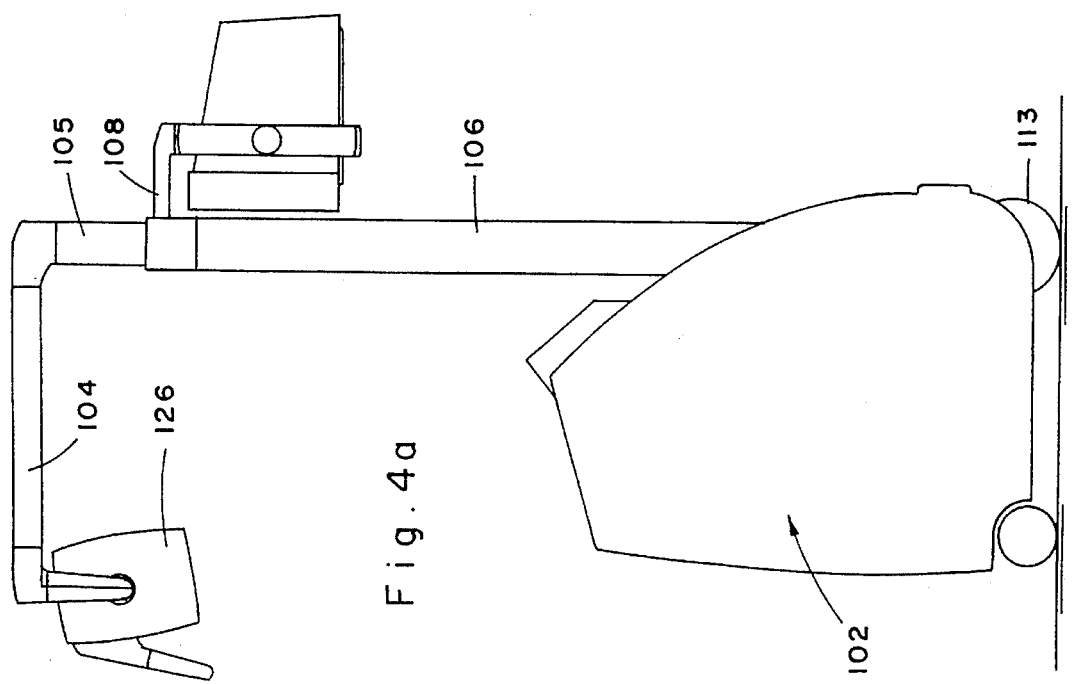

INFRA-RED VASCULAR ANGIOGRAPHY SYSTEM

FIELD OF THE INVENTION

This invention relates to an infra-red vascular angiography system and in particular, but not exclusively, to an infra-red vascular angiography system for use in cardiovascular surgery.

BACKGROUND OF THE INVENTION

The use of vascular angiography systems, particularly in cardiovascular surgery, has long been known, particularly in connection with preoperative mapping of the cardiovascular system to be operated upon for the purpose of surgical grafting or the like, and also in connection with ascertaining, after grafting, the effectiveness of the grafting, both as regards the subsequent free flow of blood through the graft to the revascularized conduit and the absence of leakage, or kindred defects.

To this end, both ultrasonic and X-ray angiography have been employed but in both cases considerable disadvantages arise, such as for example the undesirable contact between the ultrasonic probe and the exposed blood vessels, the necessity to inject into the blood vessels a suitable toxic contrast medium, and the inherent risk associated with the use of X-ray radiation.

It is as a consequence of these and other disadvantages that there has been proposed to use a cardiovascular angiographic system which is based on the thermographic technique and which involves obtaining infra-red thermal images of the relevant cardiovascular region prior to, during and subsequent to surgery. The relevant information which can be derived from such infra-red imaging arises in view of the fact that a temperature difference is established between the fluid (either cardioplegia or blood) flowing in the relevant blood vessels and the surrounding region. Thus, for example, such temperature differences can arise as a result of the initiation of fluid flow through a graft or the perfusion of blood into the surrounding tissue.

Proposals for the use of such infra-red coronary angiography have appeared in the professional literature and in this connection attention is particularly directed to the paper by Friedrich W. Mohr et al in The Annals of Thoracic Surgery, 1989; 47:441-9, entitled "Thermal Coronary Angiography: A Method for Assessing Graft Patency and Coronary Anatomy in Coronary By-pass Surgery". A proposal for a system for carrying out such angiography and clearly derived from the Mohr paper is to be found in U.S. Pat. No. 4,995,398.

These proposals have not, however, led to a practical system and have all been characterized by serious limitations which, in use, renders it impossible or difficult to employ them for real time infra-red imaging.

It is therefore an object of the present invention to provide a new and improved infra-red vascular angiography system particularly for use in cardiovascular surgery, in which the above-referred-to disadvantages are substantially reduced or overcome.

BRIEF SUMMARY OF THE INVENTION

According to the present invention there is provided an infra-red vascular angiography system comprising a readily displaceable infra-red camera including an infra-red optical assembly of high sensitivity capable of receiving and transmitting with minimal distortion an infra-red image of an object within an angular range of substantially ±45° with respect to a line perpendicular to the object; infra-red detector means for detecting the infra-red image transmitted from said optical assembly and converting it into successive electric output signals; video imaging means coupled to said detector means for digitizing said output signals and converting them into successive digitized video image frames or successive portions thereof; image processor coupled to said imaging means adapted to receive the successive video frames or portions thereof so as to process them so as to form enhanced video images and display means coupled to said image processor.

Preferably, the infra-red optical assembly comprises an infra-red lens which is adapted to be spaced from the object in a range of substantially 0.30 m to 100 m, there being furthermore provided an automatic focussing assembly for continuously maintaining in focus the infra-red image transmitted to the infra-red detector.

In accordance with a preferred embodiment of the present invention, there is furthermore provided an auxiliary portable probe for viewing and transmitting an infra-red image of a region of said object closely adjacent said probe and comprising, a housing: at least a further infra-red lens forming a window in said housing and adapted to be juxtaposed with respect to said region; a thermal fiber assembly, a first end of which is located within said housing remote from said window and a second and opposite end of which is juxtaposed with respect to said infra-red lens of said camera; and an optical system located in said housing and adapted to project an infra-red image transmitted by said window onto said first end portion of said thermal fiber assembly.

With such a system, it is possible to obtain effective real time imaging of the cardiovascular zone subject to surgery so as to have, on the one hand, an accurate presurgical mapping of the zone (thereby enabling the surgeon to determine the spot wherein anastomoses is required) and, on the other hand, to enable the surgeon to obtain in real time a clear picture of the effectiveness of the grafting which is being carried out.

Preferably, the console and the camera assembly are independently displaceable and are provided with mechanical coupling means for coupling the members together.

The camera assembly, which can be of compact construction, can be readily displaced into position during surgery whilst the console can be distanced from the operating site so as not to be in the way during surgery.

A serious problem exists for the surgeon to correlate the infra-red image observed on the member screen and relating to the region of the patient being imaged and the visible image of the same region as observed directly by the surgeon. This problem is compounded by the fact that infra-red image is intrinsically of a vague and unclear nature (even after it has been enhanced by exploiting image processing techniques) and the fact that the infra-red image necessarily includes components which, whilst emitting energy in the infra-red range, are not of interest and which, of course, cannot be seen in the corresponding visible image. It will therefore be readily appreciated that the surgeon is likely to encounter difficulties in accurately correlating the region currently being imaged with the thermal image thereof being viewed on the monitor.

It is therefore proposed to incorporate in the camera a video camera (e.g. CCD camera), thereby providing the surgeon and the assisting staff with a clear and wide video image of the precise area currently being imaged.

The incorporation of the video camera in the camera allows for two alternating display modes: a first visible display mode in which can be seen the visible image seen by the video camera (for a given field of view) and a second thermal display mode presenting a thermal image for the same field of view.

The two display modes can be alternately switched into view. When the visible display mode is operational, then the visible region being displayed can have delineated thereon, by means of suitable highlighted markings, e.g. dashed lines, the position of the corresponding thermal display zone.

Alternatively, both display modes can be simultaneously viewed, either on a split screen or with the second thermal display mode being confined to a desired limited zone within the field of view displayed by the first visible display mode.

There is thus provided in accordance with another aspect of the invention an infra-red vascular angiography system comprising a readily displaceable camera including infra-red and visible range optical assemblies and detector means; the infra-red optical assembly being of high sensitivity and being capable of receiving and transmitting with minimal distortion an infra-red image of an object within an angular range of substantially ±45° with respect to a line perpendicular to the object; the infra-red detector means being capable of detecting the infra-red image transmitted from said optical assembly and converting it into a first set of successive electric output signals; first video imaging means coupled to said detector means for digitizing said first set of output signals and converting them into a first set of successive digitized video image frames or portions thereof; the visible range optical assembly being capable of receiving and transmitting a visible image in coordination with said infra-red optical assembly and having a field of view with respect to said object which covers at least that of said infra-red assembly; the visible range detector means being capable of converting the transmitted visible image into a second set of successive electric output signals; a second video imaging means coupled to said visible range detection means for digitizing said further set of successive electric output signals into a second set of successive digitized video image frames or successive portions thereof; an image processor coupled to said first and second imaging means adapted to receive said first and second successive video frames or portions thereof so as to process them so as to form first and second sets of enhanced video images; and switching means coupled to said image processor, the latter being adapted to route either or both of said sets of enhanced video images to a display means coupled to said image processor responsive to said switching means.

Preferably, the lines of sight (LOS) of the infra-red and visible range optical assemblies coincide, in which case, of course, the respective fields of view (FOV) have a common center.

With such a system, the displaceable camera can be provided with a displacing handle carrying switching means electrically associated with the image processor means and being actuatable for switching purposes upon sensing of a contact or lack of contact with the handle. Thus, for example, when the surgeon grips the handle and displaces the camera so as to direct it onto the region of interest, the contacting of the handle automatically switches the image processor so that the visible image appears on the display means. The surgeon is thus directly guided into correctly positioning the camera. Once this has been achieved, the release of contact with the handle automatically switches the image processor so that the thermal image appears on the display means. In this way it is ensured that the visible and thermal images are wholly coordinated. Where the optical assembly provides for coincided lines of sight, the displayed visible and infra-red images always maintain a mutually coordinated spatial relationship, regardless of the position of the camera head.

Preferably, the visible range detector means, said second video imaging means and at least a portion of said visible range optical assembly are included in a video camera.

The optical assemblies can have optical components in common and among these is included a beam splitter assembly adapted to receive radiation comprising infra-red and visible range constituents; the beam splitter being adapted to separate said received radiation into an infra-red constituent directed to the infra-red assembly, and a visible range constituent directed to the visible range assembly.

In accordance with a preferred embodiment, the system comprises separate camera and console assemblies, with only the essential optical assemblies and detector means being incorporated in the camera assembly whilst the remaining, relatively bulky, components of the system being accommodated in the console assembly. The assemblies are electrically coupled together. In this way, only the relatively compact camera assembly needs to be positioned in the operating region, whilst the remaining console assembly can be located in a region where it does not interfere with the movement of the operating personnel. Preferably, the camera assembly is provided with an independent closed loop cooling system.

Preferably, the infra-red detector means is adapted to detect infra-red images at infra-red wavelength range of the order of 8 to 12 micrometers.

In accordance with a further embodiment of the invention, the image processor means includes defective cell compensator means arranged to assign compensated value to a picture element originating from a defective cell forming part of the infra-red detector means; the assigned compensated value being determined on the basis of at least one picture element value originating from a fault free cell in the proximity of the defective cell.

BRIEF SUMMARY OF THE DRAWINGS

For a better understanding of the present invention and to show how the same may be carried out in practice, reference will now be made to the accompanying drawings in which:

FIG. 4a is a side elevation of the system shown in FIG. 3.

FIG. 4b is a side elevation of a base portion of a camera head assembly forming part of the system shown in FIG. 4a when detached from the remainder of the system;

DETAILED DESCRIPTION OF SPECIFIC EMBODIMENTS

Figure 1:
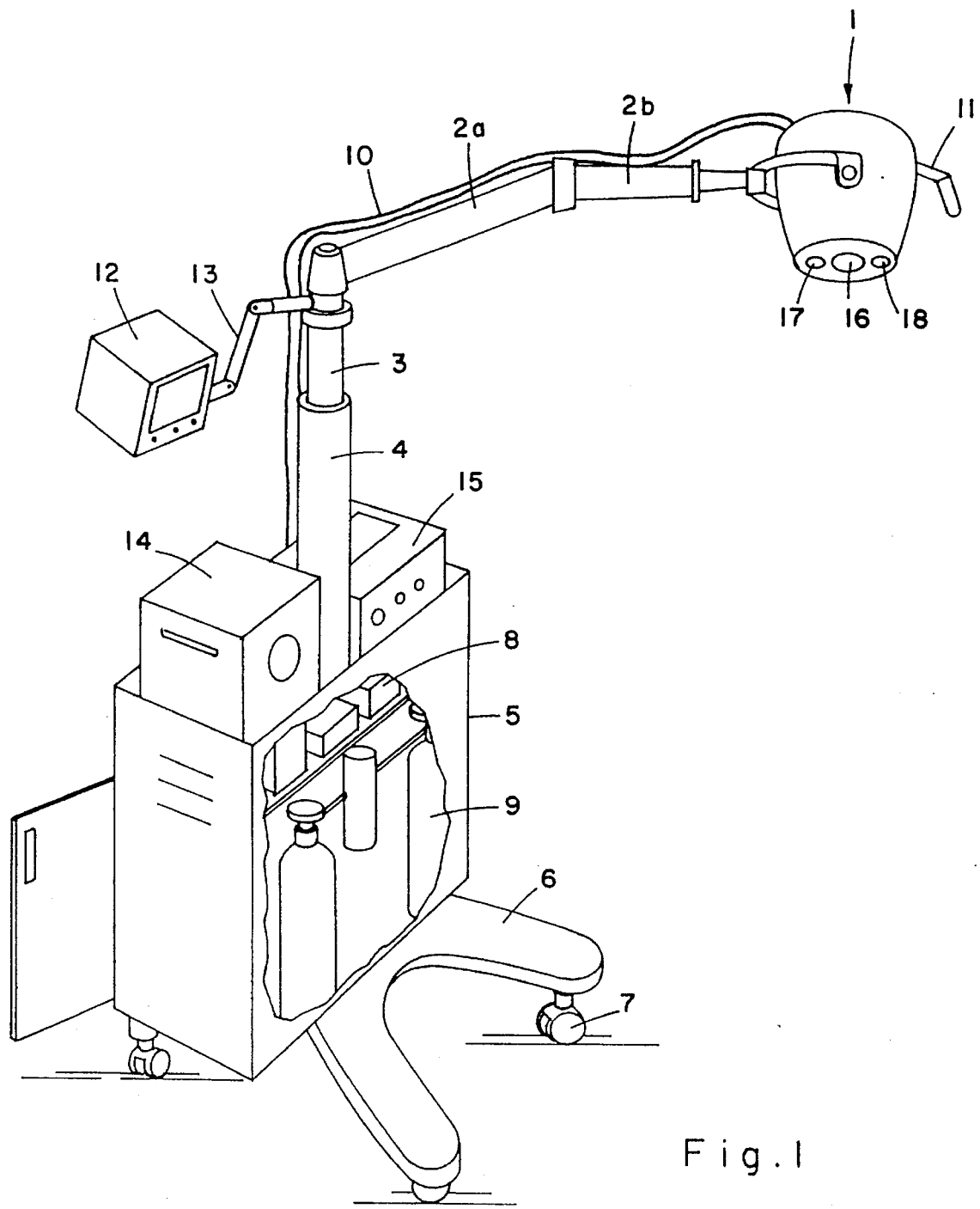
FIG. 1 is a perspective view of a first embodiment of an infra-red vascular angiography system in accordance with the present invention.

As seen in FIG. 1 of the drawings, the infra-red imaging system according to a first embodiment of the invention (referred to herein as "first embodiment of the system") comprises a thermal camera head 1 which is mounted on one end of a support arm 2 which is pivotally coupled at an opposite end thereof to a support post 3 which, in its turn, is telescopically supported within a guide sleeve 4. The guide sleeve 4 is mounted on a console cabinet 5 which is supported by legs 6 fitted with castors 7. As can be seen, the head 1 is coupled to the arm 2 so as to be pivotally rotatable with respect there to, whilst the arm 2 is, in its turn, composed of arm components 2a and 2b which are pivotally coupled together. Bearing this in mind and bearing in mind the pivotal coupling of the arm component 2a to the post 3, and the fact that the post 3 is telescopically displaceable with respect to the sleeve 4, it will be readily seen that the position of the head 1 can be readily adjusted in any required direction whilst the system, as a whole, can be readily displaced into and out of an operational position. Furthermore, it will be noted that the head is supported with respect to the console 5 in a counterbalanced position so that once the head has been placed in any required operational position, it will remain stable in that position until it is displaced into another position.

The console cabinet 5 contains, on the one hand, an electronic control module 8 for the camera head 1 and, on the other hand, high pressurized nitrogen gas containers 9, the control module 8 and the containers being coupled to the camera head 1 via appropriate coupling conduits 10.

The camera head 1 is provided with a manual adjusting handle 11 which also supports a control keypad by means of which the operation of the system can be controlled.

A monitor 12 is mounted on a suitable positioning bracket 13 which is itself mounted in a swingable manner on the support post 3. This monitor is designed to be observed by the operating surgeon and his assistant. An additional monitor 14 is supported by the console cabinet 5 and is directed to observers other than the direct operating staff. A video tape recorder 15 is supported by the console cabinet 5 for preparing a hard copy and record of the observed infra-red image.

As seen in FIG. 1, the camera head 1 has formed in its lower surface a central port 16 through which infra-red radiation can pass to an infra-red camera lens, a first auxiliary port 17 through which a marker beam can be projected for purposes to be explained below, and a second auxiliary port 18 designed to communicate with a microphone.

Figure 2:
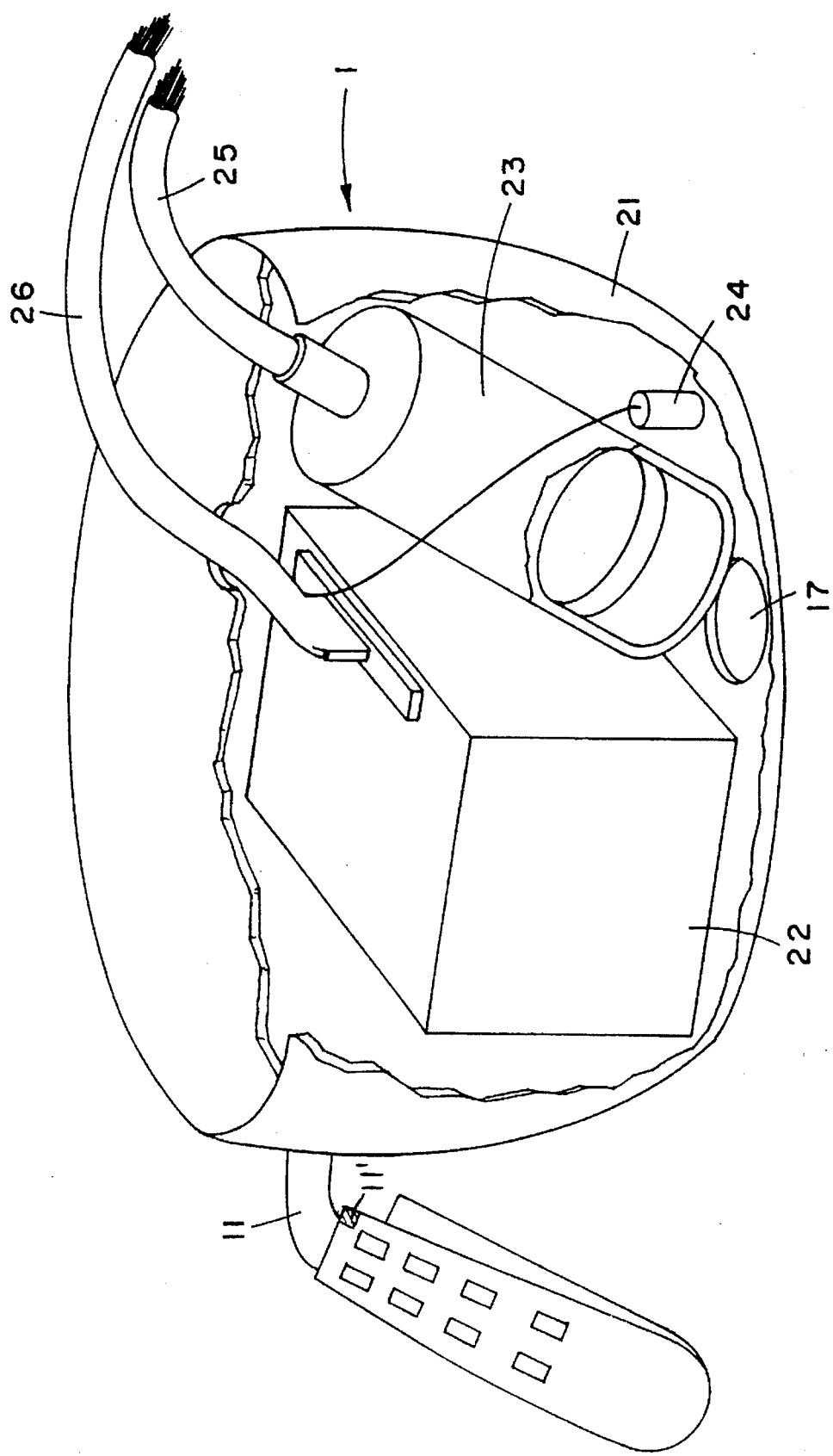
FIG. 2 is a view of the camera head shown in FIG. 1, on an enlarged scale.

The basic construction of the remote camera head 1 will now be described with reference to FIG. 2 of the drawings. As seen in this figure, the remote camera head I comprises an outer casing 21, essential camera components 22 and an optical marker assembly 23. The easing also includes a microphone 24 for use in picking up for recording, etc. the surgeon's instructions, comments or the like. The optical marker assembly 23 is coupled by means of an optical fiber bundle 25 to a light source (not shown), whilst the camera components 22 are electrically coupled via an electric cable 26 with the electronic camera control. module 8 located in the console cabinet 5.

Whilst in the first embodiment described with reference to FIGS. 1 and 2 of the drawings the described arid illustrated system involves a camera head assembly mounted on a console so as essentially to form an integral part thereof, in the embodiment shown in FIGS. 3, 4a, and 4b of the drawings the system comprises two separate units, namely a camera head assembly, on the one hand, and a console cabinet, on the other hand, which, when the system is not in operational use, can be mechanically coupled together but, when it is desired to use the system, the camera head assembly can be mechanically detached from the console cabinet and moved into position, for example adjacent an operating table, whilst the console cabinet can remain in a relatively more remote region and so does not interfere with the movement of the surgeon and his staff.

The camera head assembly 101 comprises a camera head 103 pivotally mounted on a support arm 104 which, in its turn, is pivotally mounted on a support post 105 which fits, telescopically, within a support sleeve 106. A monitor 107 is pivotally mounted via a support arm 108 to the support post 105. The camera head 103 is provided with a manual gripping handle 109.

As can be clearly seen in FIG. 4b of the drawings, the support sleeve 106 is secured at its lower end to an elongated base member 110 fitted with castors 111. The base member 110 is fitted on opposite sides thereof with rows of rotatable bearings 112 for a purpose to be explained below.

The console cabinet 102 is provided with castors 113. Formed in the lower portion of the console cabinet 102 is a compartment (not shown) into which can be slidably fitted the elongated base 110 of the camera assembly 101, means (not shown) being provided for releasably locking the base 110 within the compartment, further pedal means 118 being provided for facilitating ready detachment of the camera head assembly 101 from the console cabinet 102.

Thus, when not in operational use, the camera head assembly 101 can be mechanically coupled to the console cabinet 102 and the combined assembly can be stored wherever required. When, however, it is required to use the system, for example during a surgical operation, the camera head assembly 101 is detached from the console cabinet and wheeled into position in the region of the operating table, whilst the console cabinet 102 can remain in a relatively remote location, not interfering with the movement of the operating personnel. It will appreciated, however, that at all times during use the camera head assembly is electrically coupled to the console cabinet by electric coupling cable (not shown).

The height of the camera head 103 and monitor 107 with respect to the operating table can be readily adjusted, for example by the provision of an electric motor (not shown)

which can be actuated by the operating staff so as to bring these components into the required position. On the other hand, the angular disposition of the camera head can be adjusted using the manual operating handle 109.

In order to ensure effective cooling of the infra-red detector assembly located in the camera head, the latter is provided with an independent closed loop cooling unit and, in this way, the camera head assembly is independent of the console cabinet and there is no necessity to provide coupling fluid conduits between the console cabinet and the camera head assembly.

Figure 3:
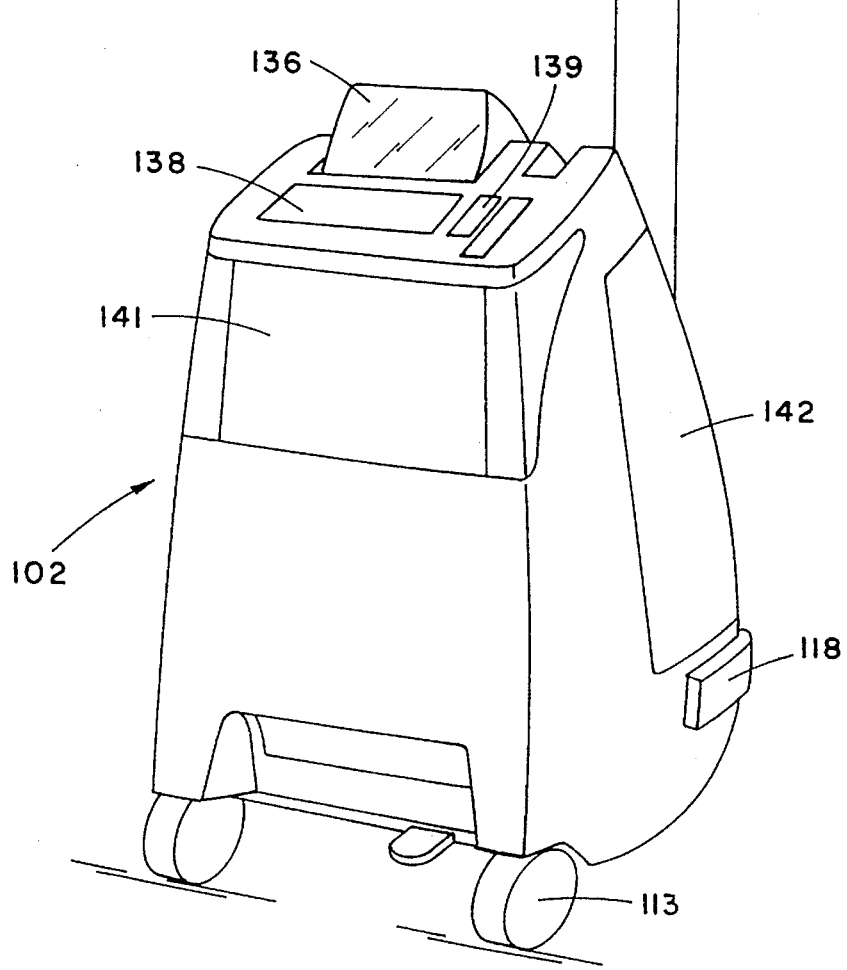
FIG. 3 is a perspective view of a second embodiment of an infra-red vascular angiography system in accordance with the present invention.
Figure 5:
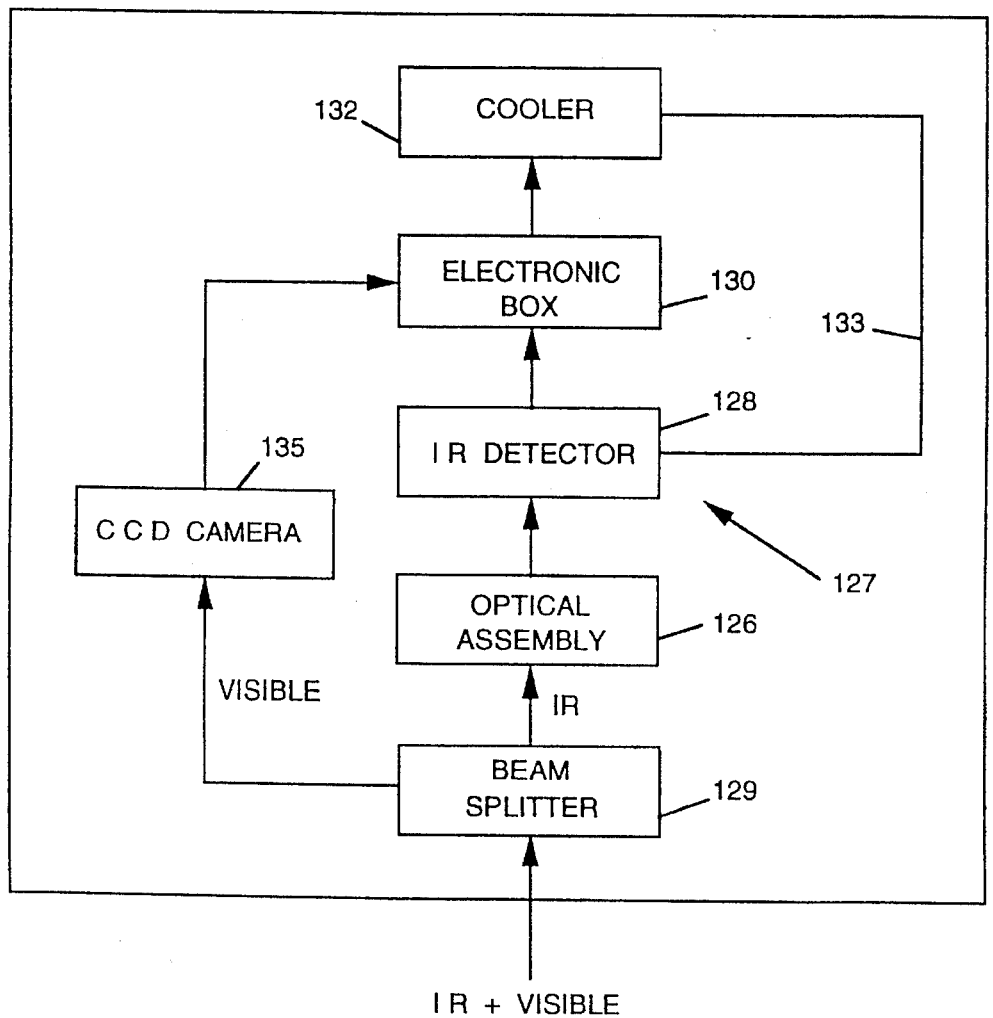
FIG. 5 is a schematic block diagram of a camera head forming part of the embodiment shown in FIG. 3.

FIG. 5 shows schematically the various components included in the camera head of the embodiment shown in FIG. 3. As seen, the camera head is provided with essential infra-red camera components designated collectively as 127, consisting of an optical assembly 126, the detector infra-red assembly 128 and an electronic box 130 (incorporating, optionally, a defective cell compensator whose operation is described in greater detail below) electrically coupled to the detector assembly 1.28. A closed loop cooling unit designated collectively as 132 is coupled to the detector assembly 128 by means of ducting means 133 so as to maintain its operational temperature at an essentially constant level.

The cooling unit 132 employed for this purpose is of compact size and silent operation. A suitable example of such a closed loop cooler unit 132 is the K523 model commercially available from Rikor Ltd., Kibbutz Ein-Harod. The camera head also comprises a CCD camera 135 which is also electrically coupled to said electronic box 130. A beam splitter assembly 129 is located adjacent an optical input of the camera head and forms part of the infra-red and visible optical assembly. The beam splitter 129 is adapted to receive radiation in the infra-red and visible wavelength ranges and to transmit to the IR camera the infra-red radiation portion whilst routing to the CCD camera, the visible image constituent. The entire operation of the various components of the beam splitter as well as the CCD camera will be explained in further detail below.

Preferably, the detected radiation may be kept within predetermined wavelength ranges, e.g. the IR constituent may be within a range of about 8–12 micrometers whilst the visible constituent may be within a range of 4–8 micrometers. This can be achieved by utilizing filtering means known per se. Such a requirement may arise seeing that other wavelength radiation ranges which are received by the optical assembly may interfere with the infra-red and visible constituents of interest, giving rise to a poor signal/noise ratio which is manifested by sub-standard displayed infra-red and visible images.

Figure 6:
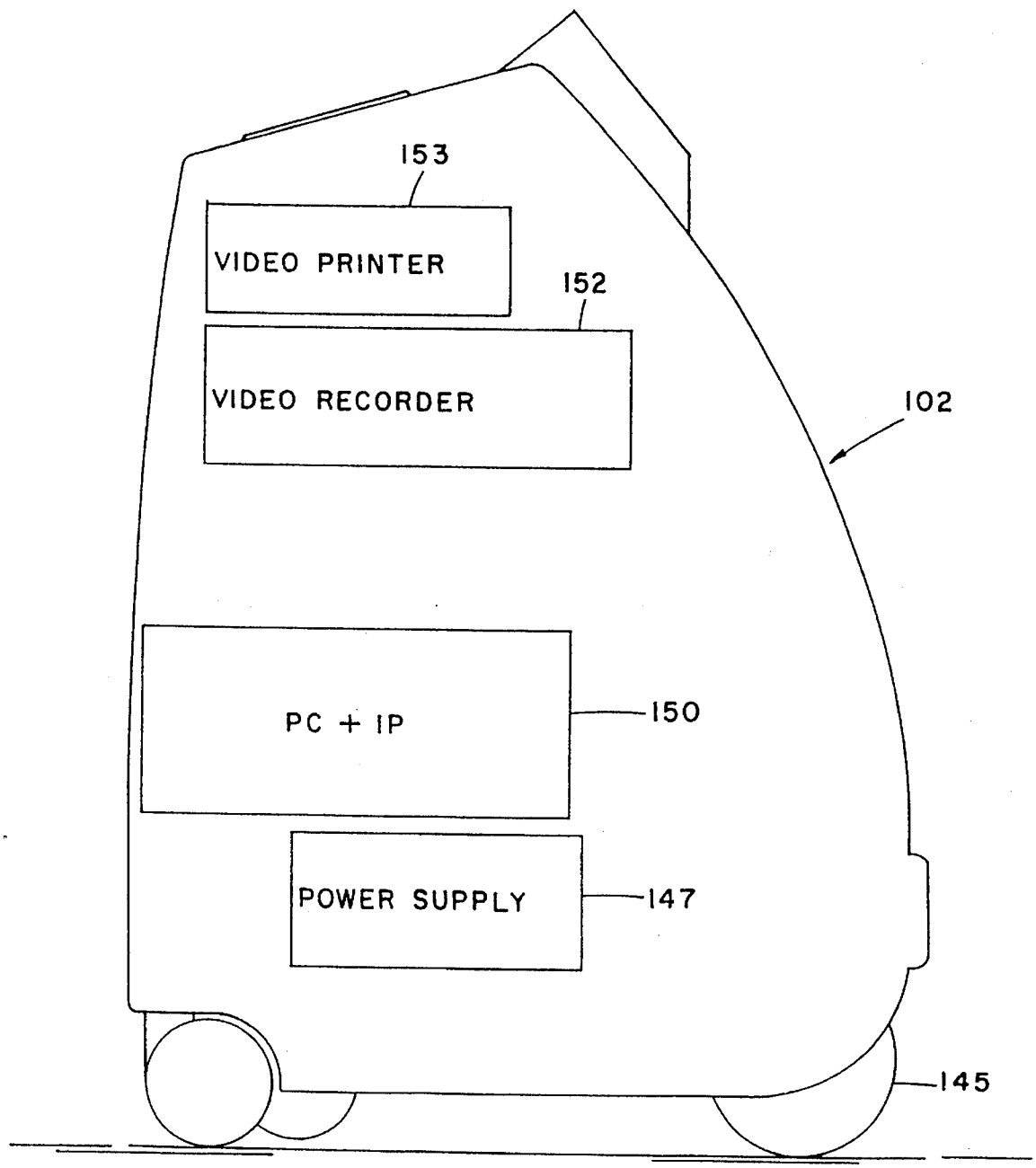
FIG. 6 is a schematic side elevation of a console cabinet forming part of the embodiment shown in FIG. 3, with the constituent components thereof shown in block form.

Attention is now directed to FIG. 6, showing schematic side elevation of the console cabinet 102 shown in FIG. 3, with the side panel removed. The console cabinet of the second embodiment of the system includes essentially the same components as those included in the console of the first embodiment of the system excluding, however, the cooling gas reservoirs. As will be appreciated by referring to FIG. 3, the upper panel of console cabinet 102 is different than that of the first embodiment of the system. More specifically, it includes an additional, built-in monitor 136 directed to observers other than the direct operating staff, a main keyboard 138 from which the entire operation of the system is controlled and a removable keyboard 139 which may be held by the surgeon or the assisting staff and provides remote control capabilities of the various functions (of the system. Also shown are doors 141 and 142, which provide for convenient access to the various components located in the console 102. The console cabinet 102 is also provided with a power supply 147 adapted to feed power to the various components of the system, personal computer board with permanent storing medium and image processing boards designated collectively 150 and serving for the image processing of the video frames as will be explained in further detail below, video printer 153 and video recorder 152 whose operations conform with those of the corresponding components of the first embodiment of the system.

Figure 7:
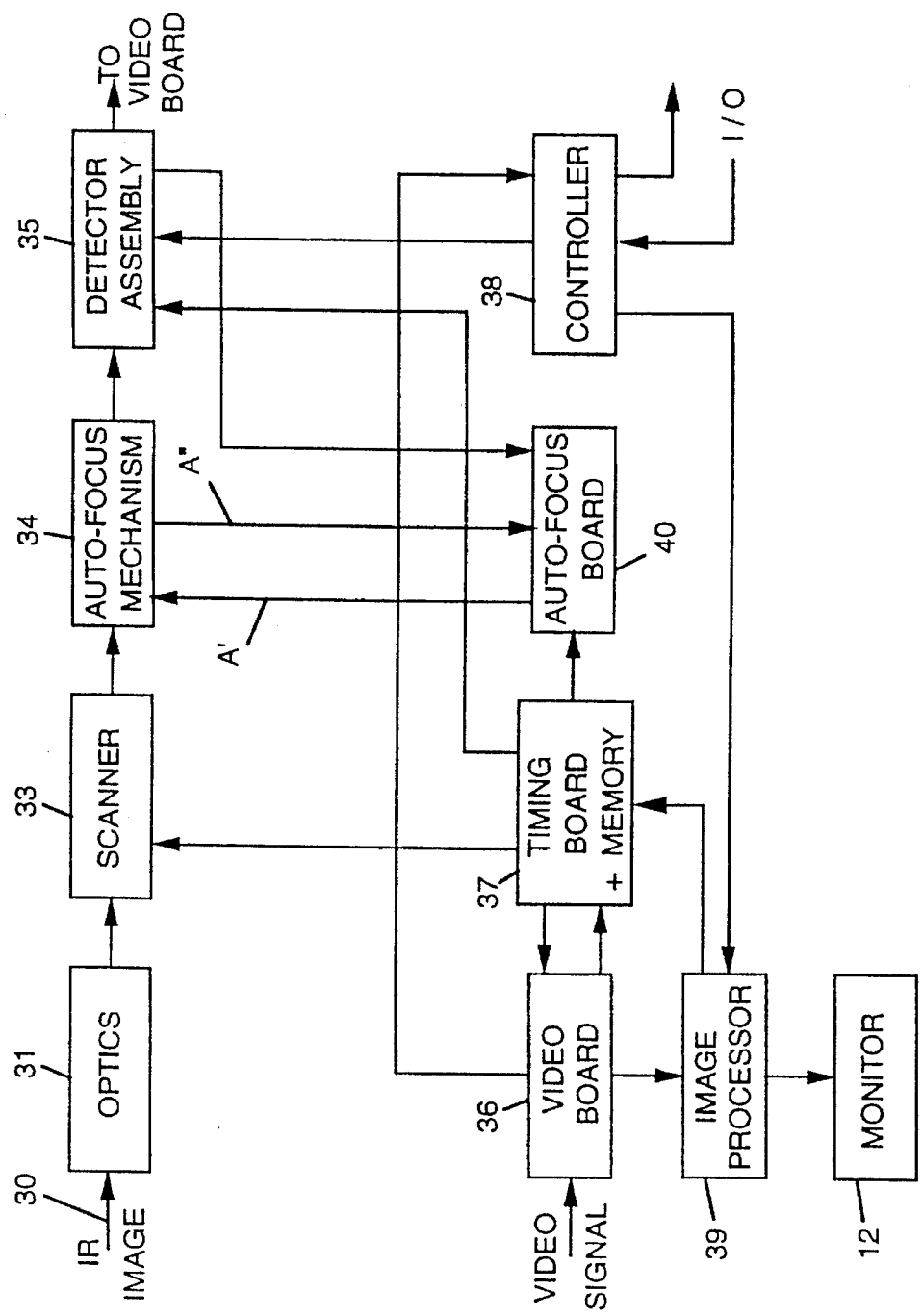
FIG. 7 is a schematic block diagram of the camera head and electronic module components utilized in the system according to the first embodiment of the invention.

Reference will now be made to FIG. 7 of the drawings, which is a schematic block diagram showing the camera components and the components of the electronic control module and the inter-connection between them according to the first embodiment of the system.

As seen in FIG. 1, the camera components 22 consist of an optical assembly 31 which is designed to transmit infra-red radiation 30 emitted from the patient. For this purpose, the optical assembly 31 in the present example consists of an at least one intern-red detector lens (preferably it comprises single lens of 500 mm focal length and appropriately made of ZnS or Ge, such as that manufactured by JANOS, Inc.), Preferably, the lens is provided with an anti-reflective coating or with separate means for reducing or preventing reflection. Such a lens is capable of transmitting infra-red radiation in the 8 to 12 μm range, this being the range which is characteristic for infra-red radiation emitted from the human body. The lens is so designed that radiation from the observed operated-upon region of the patient reaches it via the port 16. As a consequence of the use of such a lens it is possible for it to transmit, substantially undistorted, an infra-red image at an angle which can be ±45° with respect to a line perpendicular to the observed region of the patient. Thus, in this context the image is considered to be undistorted, where the edge distortion does not exceed about 10%. It will be understood that whilst in the described example a limit for the angular variation of ±45° has been specified so as to provide for minimal distortion, there may be cases wherein the user may be satisfied with a detected image with a high degree of distortion, in which case the upper limit of angular variation can be raised. Furthermore, a high resolution image can be obtained with a field depth of 3 to 6 mm at a distance of 30 cm.

This emitted radiation constitutes, in effect, an infra-red image on the object, namely the region of the patient's body which is being observed. The infra-red image transmitted by the optical system 31 is projected onto a scanner assembly 33 which progressively scans the image and projects successive scanned portions via an automatic focussing assembly 34 onto a detector assembly 35.

The automatic focussing assembly 34 is designed to ensure that the image received by the detector assembly 35 is automatically and continuously focussed, irrespective of the position of the camera. The provision of this automatic focussing assembly 34 facilitates the use of the system with the infra-red lens located within 30 to 100 cm from the region being observed. There will be described below the manner in which the automatic focussing takes place.

The detector assembly 35 consists of a linear array of appropriate infra-red detectors which are suitably cooled (to a temperature of the order of 70°–80° K.). Each of the component detectors of the detector assembly 35 is designed to convert that element of the infra-red image projected thereon into an electric signal which is subjected to appropriate filtering, pre-amplification and signal processing before being transmitted to a video board 36. Preferably, the detector assembly is constituted by individual detectors made of MCT alloy which is known for its very high sensitivity and is capable of detecting radiation variations corresponding to temperature changes of the order of 0.05° C. (NET). High resolution is obtained with temperature variations of 1° to 2° on the surface of the blood vessels. This ability of the detector to detect very small variations allows the system to be effective, e.g. widen warm cardioplegia is employed, seeing that this inherently is associated with small temperature differences.

It will be understood that the infra-red image is constituted essentially by a two-climensional matrix of basic image pixels. A typical matrix is constituted by 368×200 such pixels, whereas the detector assembly 35 consists essentially of a linear array of, for example, 128 separate detector cells. In order to transmit such a two-dimensional image to a single-dimensional detector array 35, there is utilized a scanner assembly 33 of a type which is known per se. This scantier assembly 33 comprises a suitable mirror means (not shown) which, by means of a motor (not shown), serially scans the two-dimensional image so as to transmit, during each cycle of scanning, a portion of the image corresponding to the linear array onto the detector assembly 35. This scanning continues until the entire image will have been scanned and sequentially transmitted onto the detector assembly 35.

As an alternative to the use of the detector array, it is possible to use a single detector cell, in which case the scanner assembly 33 is provided with a complex mirror system capable of serially scanning the two-dimensional image and successively projecting single image elements onto the single detector cell.

This possibility, however, carries with it the disadvantage that the lower the number of detector cells which are employed, the higher is the possibility that the presence of a defective cell will lower substantially the quality of the image obtained. Furthermore, with a very low number of cells the scanning frequency increases to such an extent as to generate a disturbing hum.

Alternatively, the use of the scanning assembly can be avoided altogether by using a suitable two-dimensional detector array having a resolution to reputable to that of the two-dimensional infra-red image.

With detector arrays (and also, of course, with the two-dimensional matrix detectors), the possibility exists that one or more of the individual detector cells will be found to be defective. In the past, and in the use of such detectors in other contexts, the existence of such individual defective cells has led to the discarding of the detector as a whole and this, of course, considerably increased the costs of the detector assemblies. It has been found that, by using a novel sampling and compensation system, it is possible to use detector arrays having a limited number of defective detector cells. Such substandard detector arrays are much less expensive than arrays where all the constituted detector cells are guaranteed to be effective. In this way the costs of the detector assemblies can be kept relatively low.

Thus, with such a defective array each defective constituent detector cell results in a video picture element of constant appearance irrespective of the radiation incident on the cell. In order to cope with this situation and obtain an observable image of relatively homogeneous quality, a process of extrapolation is employed visa vis neighboring normal and abnormal picture elements. This is effected by utilizing the "Extending Soble Filter (ESF)" method (described by Dr. M. Zucker in a thesis submitted to the University of London, Imperial College, May 1990). In accordance with the ESF method the value of the abnormal picture will be determined in accordance with the following equation $$P_d = W_1 \cdot P_{d+1} + W_2 \cdot P_{d+2} - W_n \cdot P_{d+n} + W_{n+1} \cdot P_{d-1} + W_{n+2} \cdot P_{d-2} - W_{2n} \cdot P_{d-n}$$

where $P_d$ is the new value of the defective picture element, $W_1 \ldots W_{2n}$ are weight coefficients aimed to enhance the effect of the proximal picture elements and diminish the effect of the distal ones. $P_{d-n}-P_{d+n}$ are the neighboring picture elements with small n values denoting proximal picture elements and large n values denoting distal ones. n may be selected in accordance with the particular circumstances as elaborated in the aforesaid reference. The term "value" of the abnormal picture means the grey level to which it will be set or to the color, whichever the case may be. Other techniques may be employed to achieve the same result.

The signal appearing at the output of the detector assembly 35, which is effectively a video signal having been subjected to amplification and noise filtering as well as to preliminary processing, is transmitted from the camera head 1 via suitable wiring to an input of the video board 36 forming part of the electronic control module. The video board 36 is effective in converting the video signal to a digital signal. The video board 36 is coupled to a timing board and memory 37 and to a controller 38, and in this way there is formed a video frame which is fed from the video board 36 to an image processor 39, and from there to the monitor 12. The video board 36 and the controller 38 are also designed to achieve line interlacing and the production of various timing signals such as "end of line" and "end of frame" signals, and result in the conversion of the video process signal into a required video standard such as PAL, SECAM, etc. The "end of line" signal is utilized by timing board 37 to instruct the scanner assembly 33 to scan successive image sequences and also to instruct the detector assembly to transmit to the video board 36 the next video line signal which corresponds to the next frame segment. The controller 38 is fed with "end of frame" signals which serve also to incorporate indication and error messages in the frame shown in the monitor. It will be understood that the provision of these boards and controller and their mode of operation are standard in the art and will therefore not be described in any further detail.

There is furthermore provided an automatic focussing board 40 which, as seen, is electrically coupled, on the one hand, to the automatic focussing assembly 34 and the detector assembly 35 and, on the other hand, is coupled to the output of the timing board 37 and the input of the controller 38. The purpose of the automatic focussing board 40 is to control the operation of a d.c. motor (not shown) located within the camera head 1 and which, in its turn, is responsible for the displacement of a moveable focussing lens (not shown). The automatic foccussing board 40 receives and essentially samples a video signal received from the detector assembly 35 and which corresponds to a particular position of the focussing lens. The automatic focussing board 40 continues to sample this signal as the focussing lens is shifted under the influence of the motor in accordance with signals transmitted to the motor from the automatic focussing board 40 in a closed loop fashion schematically shown by lines A'-A", and this sampling continues until the video signal received by the automatic focussing board 40 is optimal in terms of signal to noise ratio. This procedure of focussing lens positioning is ongoing and therefore, at any stage, when the camera head 1 is displaced into a new position the automatic focussing assembly 34, in association with the automatic focussing board 40, will displace the focussing lens such that an optimal video signal is generated.

Such an automatic focussing mechanism 34 and its associated automatic focussing board 40 arc known per se. Whilst in the arrangement and mode of operation just described sampling of the signal as a whole takes place, it will be understood that it is possible to carry out automatic focussing by sampling only those signals which correspond to the frame center and to average them. For this purpose, the automatic focussing lens is placed in that position which corresponds to a "highest average" which is obtained. In this connection, and so as to ensure that the automatic focussing mechanism is synchronized with the sampling of the image segment located in the center, the automatic focussing board 40 is electrically coupled to the timing board 37 which, due to the "end of line" signals received from the video board 36, triggers the automatic focussing board 40 when the center of the frame is scanned.

The use of the automatic focussing assembly allows for the obtaining of a clear image even when the camera is located at the minimum distance from the observed region (~30 cm). Also a field depth of the order of 3 to 6 mm can be achieved at this minimum distance.

Figure 8:
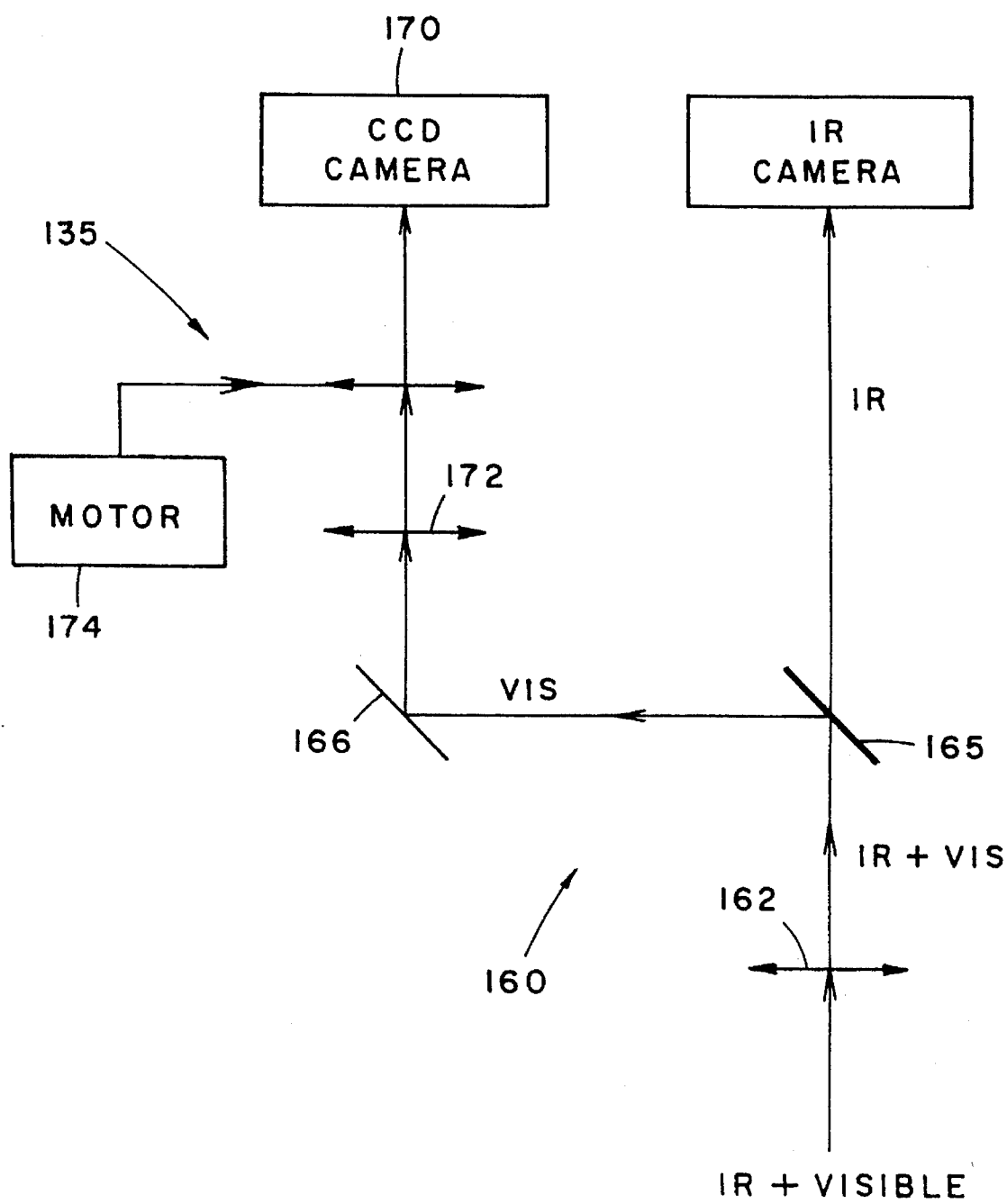
FIG. 8 is a view on an enlarged scale of a beam splitter assembly incorporated in the camera head as shown in FIG. 5.

As previously explained, in the system according to the second embodiment the camera head is designed to receive images from the same or overlapping fields of view, both in the visible and infra-red ranges. Attention is now directed to FIG. 8 for a description of the operation of this system.

An optical assembly designated collectively 160 comprises a lens 162 of the same general kind as that utilized by the first embodiment of the system with the exception that in this second embodiment of the system the lens is also adapted to receive and transmit visible wavelengths radiation. The visible and the infra-red radiation is incident on a tilted lens 165 which, in its turn, transmits the IR image constituent to the IR camera for further processing, whereas the visible image constituent is reflected onto a mirror 166 which projects it onto the CCD camera 135. The lenses 162, 165 and mirror 166 form, in fact, the said beam splitter (129).

Thus, by virtue of the use of this beam splitter assembly it is ensured that both the visible and infra-red radiation detected by the camera originate from fields of view having a common center and that, in consequence, the observed infra-red and visible range images are associated with the same region of interest of the object, regardless of the position of the camera head.

It should be nevertheless stressed that the beam splitter arrangement just described is merely an example and other beam splitter arrangements may be equally well employed for the same purpose. Furthermore, the system can be designed where the fields of view do not have a common center, but in this case provision has to be made for appropriate coordination by the use of coordinator process means.

The CCD camera assembly 135 comprises, in this embodiment, a commercially available CCD camera 170 (e.g. model XC999, commercially available from Sony Inc. Japan), fitted with a movable lens 172 and a focussing D.C. motor 174 coupled thereto, both of which constitute in fact the auto-focussing mechanism associated with the CCD camera. The optical assembly may be associated also with fine adjustment means (not shown) facilitating fine displacement of one or more constituent members of the optical assembly in case of undesired displacement of one FOV center with respect to the other, thereby restoring the desired coincidence of the FOV centers.

Turning again to the auto-focussing mechanism, it is realized that in addition to the auto-focussing mechanism incorporated in the infra-red camera, there is also available a distinct auto-focussing mechanism serving the same purpose with regard to the CCD camera and which operates in essentially the same manner.

By virtue of the inherently clearer image of the visible radiation range, it is easier to obtain the desired auto-focussing effect by applying it to the visible image rather than to the infra-red image, and once the visible image is rendered in focus it is possible to derive in a manner known per se a compensating coefficient which will readily give rise to the precise displacement of the infra-red movable focussing lens (incorporated in the auto-focussing mechanism 34, FIG. 7) which is required in order to place the infra-red acquired image in focus. The control for the visible image auto-focussing may also be incorporated in a board 40 but this, of course, is not obligatory and a separate control board may be utilized for this purpose. The value of the compensating coefficient is closely related to the geometrical and optical parameters of the infra-red and visible optical assemblies, such as, for example, the distance between the respective optical assemblies, the optical path difference between the IR beams used to form the IR image and the visible beams used to form the visible image.

In other words, by this preferred embodiment The auto-focussing mechanism employed for the production of the infra-red image is enslaved to that employed for producing the visible image. As will be explained in further detail below, in this way a clear and precise display is obtainable of either or both of the infra-red and video images originating from the treated region. Alternatively, the auto-focussing mechanism associated with the CCD and IR cameras operate independently of each other.

It is to be understood that an important feature of the system in accordance with the present invention is that the camera head is kept as compact as possible. This is achieved in accordance with the description by, on the one hand, utilizing an optical assembly which consists of a flat lens and, on the other hand, by ensuring that the electronic control module is located remote from the head. The compactness of the head can, however, be still further enhanced by removing all elements from the head other than the infra-red lens and locating them in a remote location to which the lens is optically coupled by optical fiber means. Even in the case where, as in the second embodiment, the camera head has to accommodate the closed loop cooling system, the camera head is still relatively compact and the fact that the camera head assembly is kept separate during use from the console cabinet still ensures that minimum space is taken by those elements of the system which are kept in the operating region.

Figure 9:
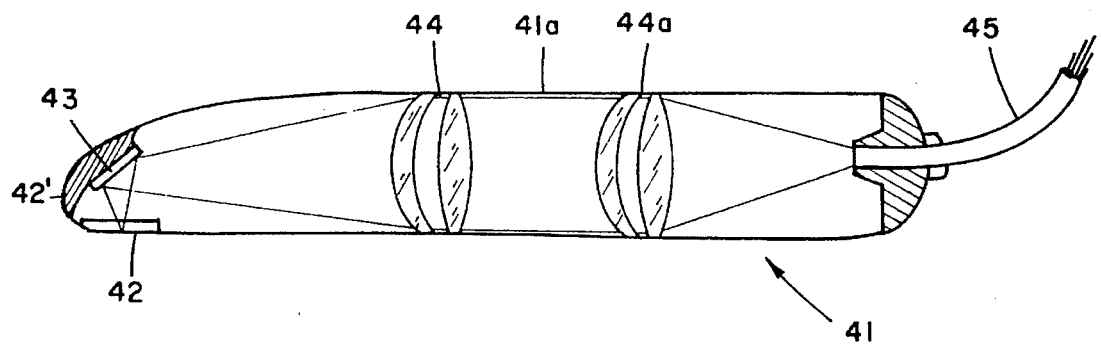
FIG. 9 is a longitudinally-sectioned view of a first form of auxiliary portable probe for use with the system in accordance with the invention.
Figure 11:
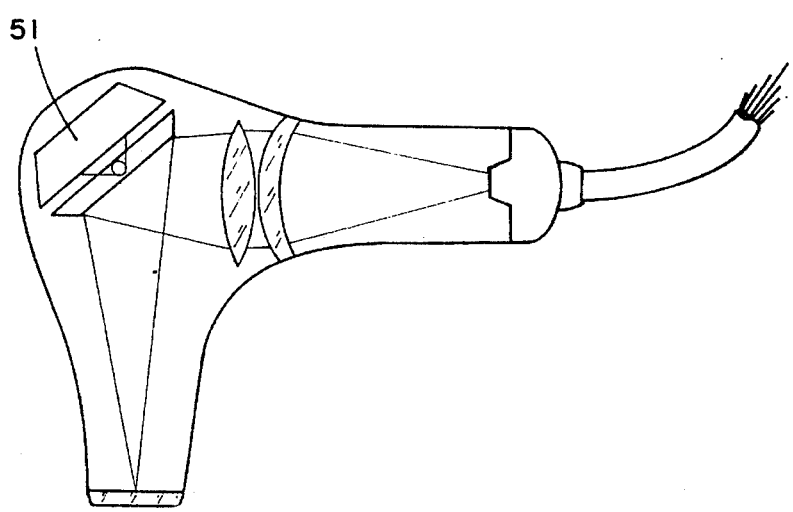
FIG. 11 is a longitudinally-cross-sectioned view of a second form of auxiliary portable probe for use with the system in accordance with the invention.
Figure 10:
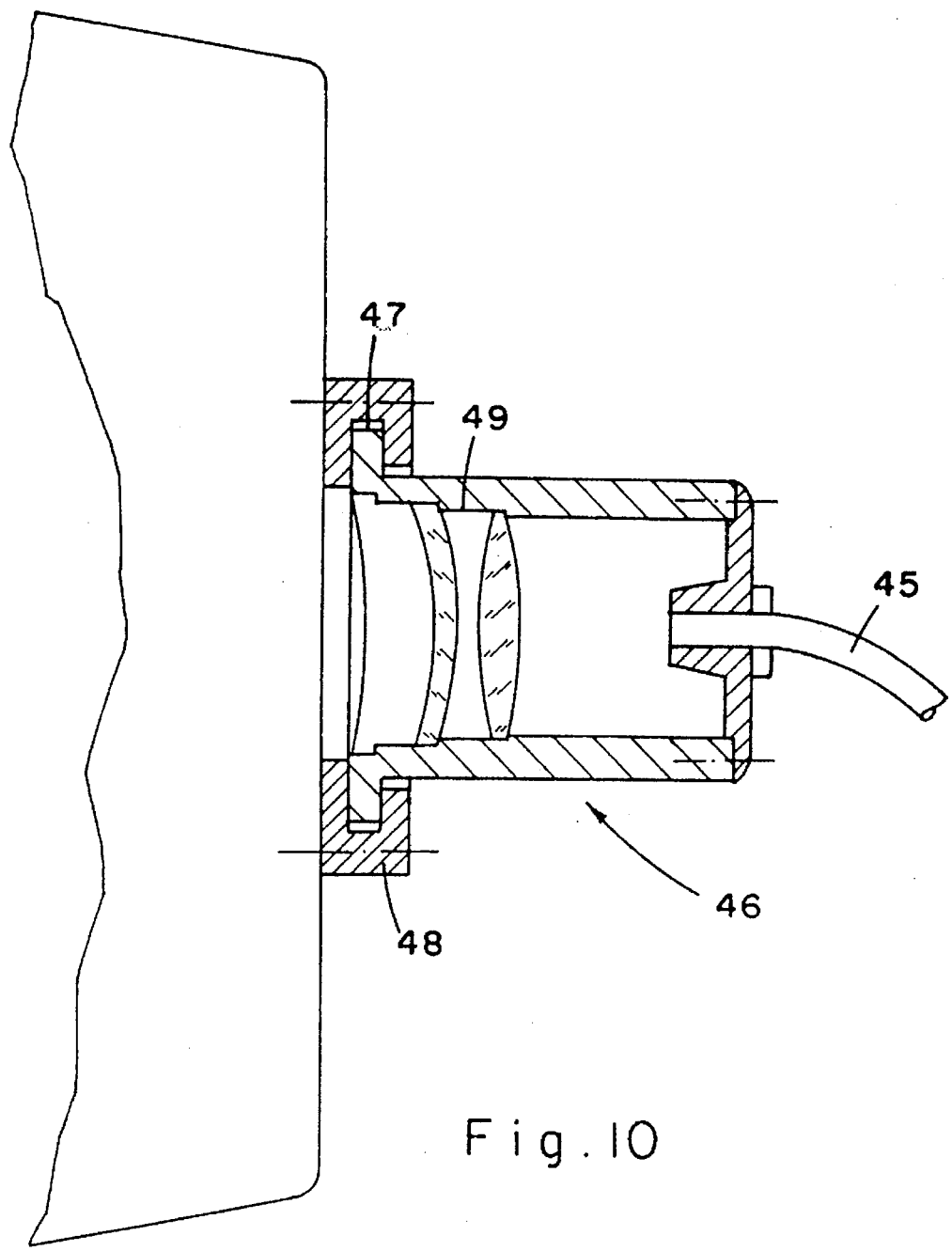
FIG. 10 is a cross-sectional view of a coupling unit for coupling to a camera bead the probe shown in FIG. 9.

Regardless of whether the first or the second embodiment of the systems is employed, the invention further provides for the use of an auxiliary infra-red probe as illustrated in FIGS. 9 to 11. Focussing at first on FIG. 9, an elongated, substantially cylindrical probe 41 comprises a tubular housing 41a having at its front end an infra-red window 42 made of either Ge or ZnS alloy. The infra-red image sensed by the infra-red window 42 is projected onto a mirror means 43 which in turn directs the image onto a lens system 44, 44a which serves for amplification and the focussing of the image onto a bundle of optical fibers 45 protruding from the housing 42. The number of fibers in said bundle equals the number of picture elements of the infra-rad image such that each picture element is transmitted via a distinct fiber. In this manner the entire image is transmitted simultaneously by the optical fibers. The opposite end of the fiber bundle 45 is secured to a coupling unit 46 which is shown in FIG. 10. The coupling unit 46 is provided with means 47 (e.g. a bayonet coupling) by means of which it can readily and releasably be coupled to an appropriate location 48 in the camera housing adjacent the infra-red camera lens. The coupling unit 46 in turn includes optical lenses 49 which expand the image conveyed by the optical fibers to an image positioned in the focal plane.

With such a probe it is possible to obtain an infra-red image of a selected zone which would otherwise be outside the camera's field of view. This has a significant importance when, for example, it is desired to view a rear of an organ which, for medical reasons, cannot be displaced so as to expose it to the camera. With the probe it will be possible to obtain the desired image without interfering with the organ's normal functioning. Obviously, all the advanced image processing features described hereinbefore are also feasible with the image obtained from the probe means. Additionally, it is possible to obtain an in fra-red image from very close proximity, i.e. much less than the 30 cm which is the minimal distance of the infra-red camera. It is thus appreciated that the use of probe means constitutes a significant advantage by providing the surgeon with an auxiliary tool which enables him to obtain an infrared image at any desired distance.

In an alternative embodiment, the probe may be permanently coupled by the optical fiber bundle to the infra-red camera. The probe may be provided with several infra-red windows (e.g. additional window situated at section 42' of the probe's housing that is illustrated in FIG. 9) enabling the surgeon to view images from various directions. Alternatively, by aligning the infra-red window with the optical system 44, 45, the infra-red image transmitted by the window can be projected directly onto the exposed fiber bundle end without the necessity of using a reflecting mirror.

In the embodiment shown in FIG. 11, the probe is provided with a scanner assembly 51 similar to the scanner assembly 33 of the camera head 1. This facilitates the projection of discrete image signals onto a relatively limited number of optical fibers and in this way the size of the optical fiber bundle can be reduced.

The ability of the probe to transmit an infra-red image when located extremely close to the object arises out of the optical characteristics of the window lens and in particular out of the focal length thereof. Similar to the arrangement with the main camera, the probe can also be provided with an automatic focussing mechanism.

Figure 12:
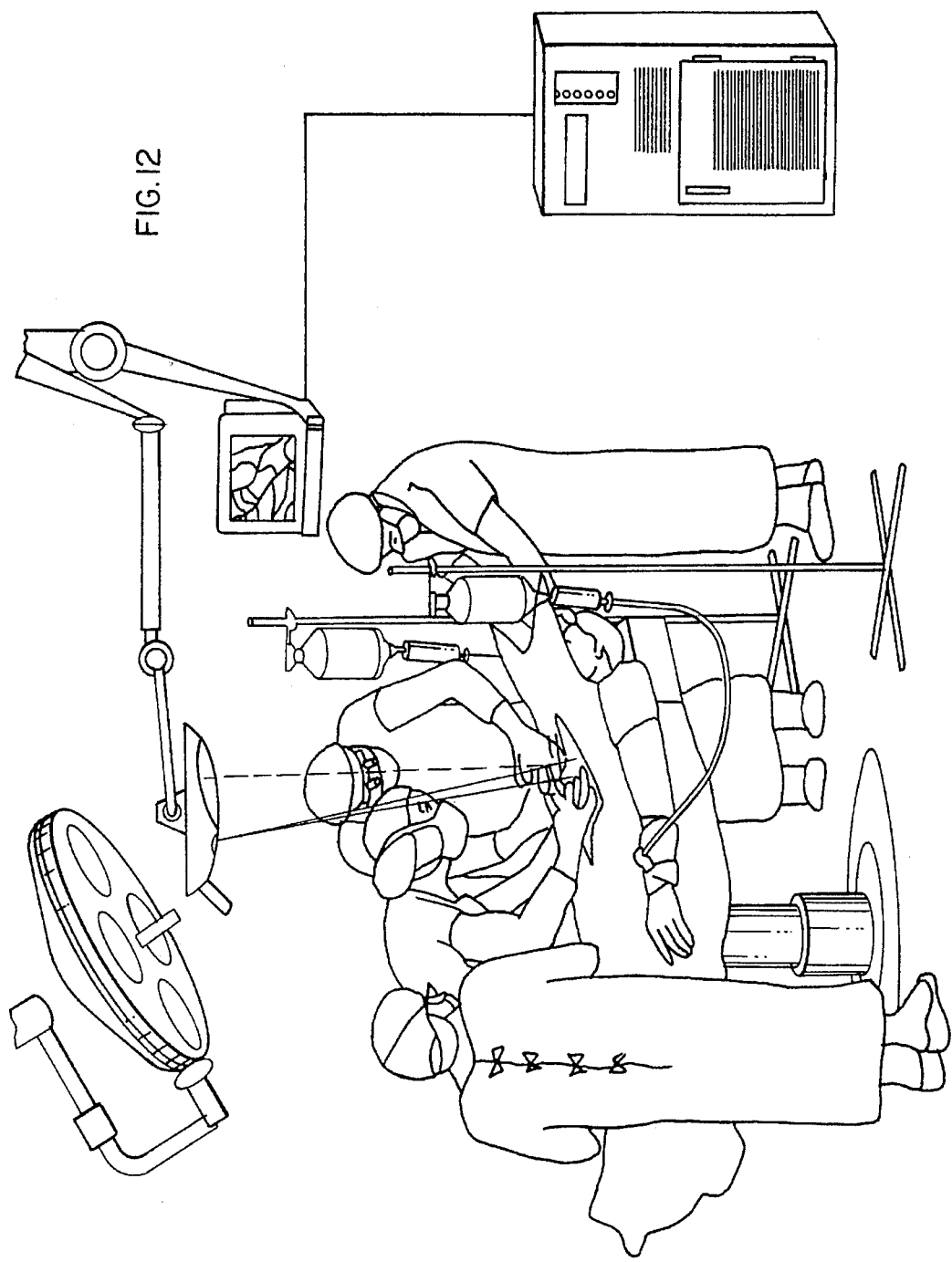
FIG. 12 is an illustration of the system in operation during cardiovascular surgery.

Reference will now be made to FIG. 12 of the drawings, which illustrates the use of the system according to the embodiment of FIG. 1 in intra-operative vascular angiography. As seen in this drawing, the remote camera head is located directly above a patient undergoing vascular surgery with the infra-red lens receiving infra-red radiation from the exposed blood vessels of the patient. At the same time, a video camera is viewing a light beam of predetermined shape onto the region of the blood vessels whose infra-red image is received by the lens, thereby enabling the surgeon to adjust the position of the camera (and of the light marker) to that region whose infra-red image is to be shown on the monitor. This adjustment is effected by the surgeon, or his assistants, using the manual handle 11. As was previously indicated, the handle 11 is provided with a control keypad which controls the electronic and possibly pneumatic operation of the system. This keypad is, of course, readily accessible to the surgeon or his assistants, who can use it at all times to select the appropriate adjustments and modifications. It will furthermore be realized that the handle and keypad can easily be maintained in a sterile condition.

By infra-red imaging the presence and/or flow of blood and/or cardioplegia liquids (either cooled or warm), it is possible to obtain at any desired instant an infra-red image of the blood vessels and thereby to obtain a preliminary mapping of the blood vessels and, after surgery, to determine the effectiveness of the grafting and the associated anastomosis and also any perfusion-related phenomena. As already indicated, the use of the particular infra-red lens and the use of the automatic focussing assembly allows for the placing of the camera head in a wide range of positions (a 45° deviation from the perpendicular and a distance from the exposed blood cells ranging between 30 to 100 cm).

In accordance with all the various possibilities referred to above, a clever infra-red image is obtained with a wide field of view which is preferably chosen to be of 4° to 6°. With such a field of view, the resolution which is obtained on the observed surface is substantially 0.1 mm when the camera head is spaced 30 to 40 cm from the observed region.

The displacement of the camera head may be effected mechanically, or may be pneumatically or electrically controlled. At all stages, the surgeon can observe the infra-red image on the monitor and the image can, as required, be recorded on the video recorder. The image processing unit can be adapted to operate in the known "windowing" technique in which only selected segments of the viewed frame are subject to signal processing. It should be borne in mind that due to the high memory requirements of a video frame (of the order of 70 Kbytes), only a limited number (10–100 frames) are stored simultaneously in the memory and the image processor must have a capacity capable of accommodating the rate of the incoming video frames, which is typically 30 frames per second.

Furthermore, it is preferably desired to complete the processing relating to a given frame prior to receiving the succeeding one, so that the computed data related thereto may be shown on the screen. This is not an essential requirement and there may be other solutions, such as buffering means, for temporarily storing the succeeding frame In any case, the system should preferably be adapted for working in a real time environment, which entails that the processing time per frame does not exceed approximately 33 msec. To this end, the windowing technique is suitable since it is only required to process the sub-image defined by the window.

The image processing unit also provides for "move window" and "window resize" functions.

In accordance with an alternative embodiment, the image processor can have larger memory banks for storing hundreds of frames and one or more powerful Data Signal Processors which will serve for accelerated calculation, though this would result in a more cumbersome and a relatively expensive unit.

The frame may be displayed either in color or in black and white. In the latter, black represents "cold temperature" whereas white represents "hot temperature". The grey levels in between the extreme black and white values are associated with the temperature range between the cold and hot extremes. The cold and hot extremes may vary from image to image and, in consequence, the intermediate grey levels will automatically be adjusted to the corresponding temperature range. Where there is a color representation, various shades will represent the different temperature ranges.

X Y coordinates can also be incorporated in the displayed image for reference purposes. The orientation of the X Y coordinates may be selected by the surgeon. Thus, by way of example, the surgeon may choose the Y coordinate to coincide with the patient's legs→head direction or alternatively he may choose to set the Y coordinate in such a manner that it will coincide with his line of sight. This flexibility will help the surgeon to correlate readily between the represented image and the location of the site from which this image is taken.

By arranging for the representation of a reference grid on the monitor screen it is possible to determine the size of the blood vessels or any other component of the infra-red image.

The image processor can be provided with automatic gain control (AGC) so as to ensure that at all times differing maximum temperature ranges are effectively observed and that thermal saturation with consequent failure to distinguish at all times between differing temperatures at range extremities is avoided. Thus, for example, with 8 BIT representation where the lowest representative of the temperature range is associated with 0 (hexadecimal representation) whilst the highest representative is associated with the value FF (hexadecimal representation) with the intermediate representatives associated with the remaining 1 to FE (hexadecimal representation) values. The image processor can also provide for extraction and subtraction of background in order to enhance and isolate the desired image in the window selected by the surgeon. It is also possible to carry out in a known manner Frame summation so as to improve signal to noise inside the window. The AGC may be ensured by the image processor 39 whose operation will be explained in further detail below.

A modified image processor unit for use with the second embodiment of the system will now be described with reference to FIG. 13, which is a schematic block diagram of the image processing components as well as the video camera and monitor devices associated therewith.

Figure 13:
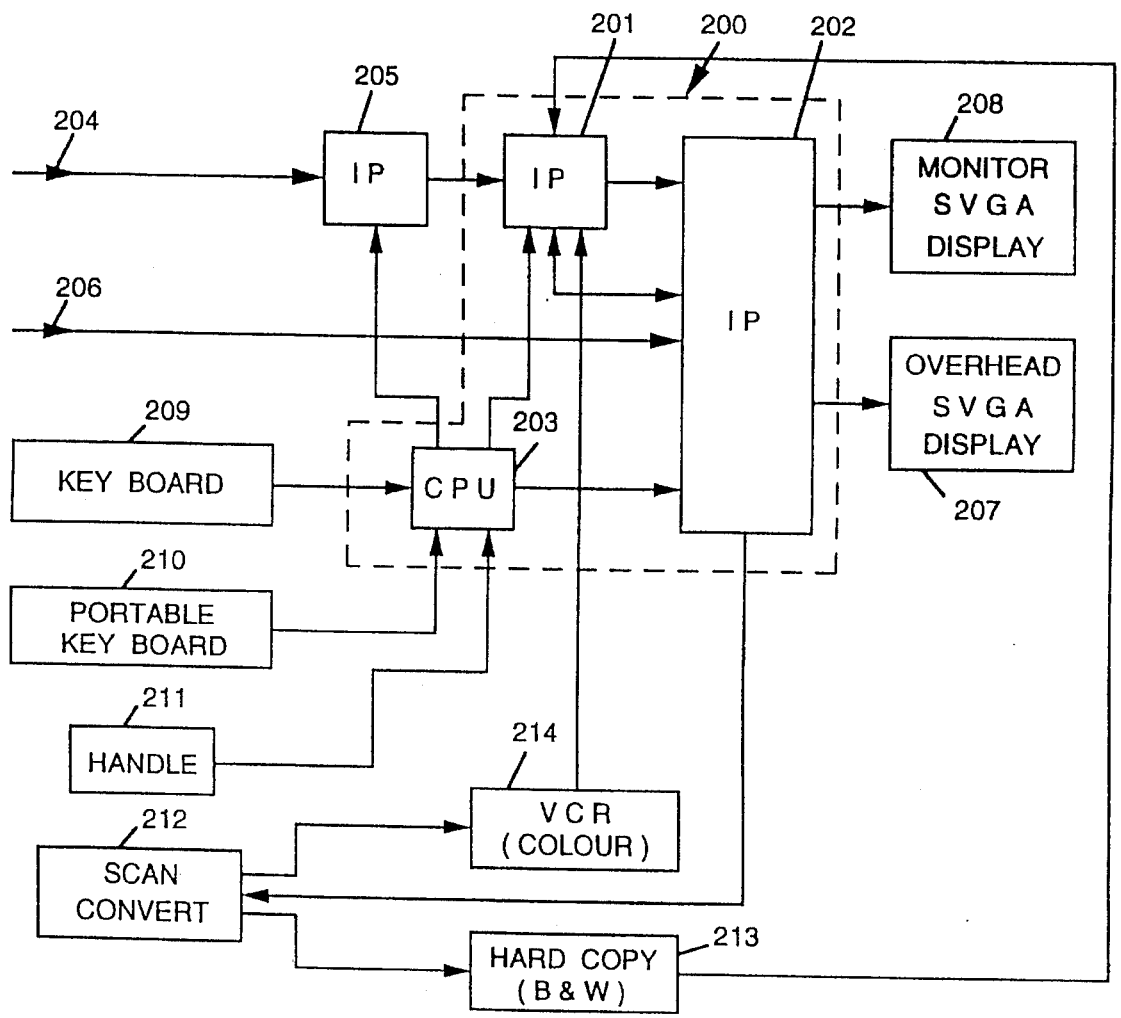
FIG. 13 is a schematic block diagram of image processor components and VCR and monitor devices associated therewith, forming part of the system shown in FIG. 3.

As seen in FIG. 13 of the drawings, an image processor unit, designated collectively as 200, comprises first and second image processing blocks 201 and 202 and a central processing unit 203. A first set of digitized (IR) video image frames is fed from an input 203 via a third image processing block 205 to the first image processing 201. The function of the third image processing block 205 is to effect defective cell compensation in accordance with the ESF technique described above. This particular defective cell compensation technique has been described merely by way of example and the desired compensation may be effected by various other known techniques, such as, for example, bi-linear transformation. Moreover, the neighboring picture element which contributes to the formation of the estimated value of the video picture element corresponding to the defective cell, need not necessarily be taken from the same video line, but can be taken from neighboring lines. The second set of digitized video image frames (visible range) is fed from an input 205 directly to the second image processing block 202. The video signals, therefore, originating from the infra-red camera arriving at the image processing block 201 undergo image processing of the kind described above and proceed to the second image processing block 202 which, as indicated, is also fed with the second visible range video image signal input. This second image processing block 202 is, in fact, a display board capable of routing either or both of the first and second digitized video image signals to either or both of display means 207 and 208, the former being an overhead display means capable of being directly viewed by the surgeon and the latter being a monitor display means which can be viewed by auxiliary members of the operating staff.

The entire operation of the image processing module 200 is controlled by the central processing unit 203 which, for example, is of a type 80486 which can be procured commercially from Intel, Inc. This central processing unit 203 operates under the control of suitable software stored on permanent storing medium, for example a hard disk (not shown).

The operation of the central processing unit 203 as far as the switching between the visible and infra-red modes of operation is concerned, is controlled by switching means (indicated generally as 11' in FIG. 2 and which could stand for e.g. known per se micro-switch or optical switch) which, as described, are automatically actuated by gripping or releasing the handle 211. The operation of the control processing unit 203 as regards the various features afforded by the image processor, is controlled by either or both of the permanent keyboard 209 and portable keyboard 210. Thus, The former is used to record data such as, for example the name of the patient, the names of the surgeon and the assisting staff. The portable keyboard, on the other hand, can be used during the operation for instructing the central processor unit and its associated image processor to perform a desired action, e.g. to form blood flow and blood perfusion rates calculations, etc.

It will be understood that in. view of the fact that the first digitized video image signals (IR) originating from the infra-red camera are in the form which comply with common infra-red standards (such as RS170), whilst the second digitized video image signals (in the visible range) originating from the CCD camera are in the form which comply with known video standards (such as NTSC), these signals must, prior to being fed to the appropriate display means, be coordinated into common form. This is achieved by the second image processing block 202, by appropriate standards conformation in a manner known per The second image processing block 202 can also be used in order to feed to the display appropriate headings and titles, an indication of the XY coordinates and, among other things, providing a grid on the display screen.

As can be seen, a further output from the second image processing block 202 is fed to a scan converter 212 capable of converting the input from a super video image adapter (SVGA) representation to a video representation capable of being recorded on a standard VCR device (as described above with reference to FIG. 6) or, if desired, to obtain therefrom a hard copy 213 of the picture currently being inspected. As can be seen, the hard copy output 213 can be fed to the first image processing block 201 so as to obtain the representation thereof on an SVGA monitor display. In this way, it is possible to obtain a clear display of the hard copy picture. As indicated above, the output from the scan converter 202 which, as has been explained, is fed to produce the hard copy 213, can also be fed to the VCR recorder where a permanent record can be made of the ongoing infra-red imaging. As can be seen, an output from the VCR recorder 214 is fed to the first image processing block 201 and, in consequence, the recording, after having been subjected to the appropriate image processing by the image processing unit 200, can be viewed on one or other of the displays, thereby facilitating a post factum analysis of the operation long after the operation has been terminated.

It will be understood that the display of the thermal and visible range images must be coordinated i.e. the images must originate from the same region and must be observed on the basis of corresponding fields of view. To this end it must be ensured that the region which gives rise to the thermal image must lie wholly within the region giving rise to the visible range image and that there is maintained a constant spatial relationship between the two regions.

The desired display mode is selected by the surgeon or the assisting staff, by a suitable command from the main keyboard 209 or from the portable keyboard 210. The system is also designed to automatically switch into a visible range display mode whenever the surgeon grips the camera head handle 211 and moves the camera head to the desired position. This, as already specified, will assist in fast identification of an area of interest, anti upon bringing the camera head into the desired position and release of the handle, the image processor 202 automatically switches into the thermal mode by which the thermal representation of the area currently under inspection is fed to and shown on the display. Where the IR field of view is located within the visible range field of view the boundaries of the former are constantly marked on the visible presentation so the surgeon is capable of determining at each particular moment during the visible display mode, the zone which will be displayed in thermal mode once he releases the operating handle.

The implementation of the aforesaid feature is effected with the aid of the switching means fitted within said handle which, responsive to sensing contact (or absence of contact), initiates a suitable command to the central processing unit 203, which in turn instructs the image processor 202 to route either the signal representative of the visible image or, alternatively, the signal indicative of the thermal image. Such sensing means may be, for example, in the form of micro-switch, optical sensors, audio actuated switch and other means all as known per se.

If desired, it is possible to initiate a suitable command from one of the keyboards so as to obtain a split-screen presentation showing at the same time a thermal image representation and a corresponding visible representation. The examples just described of the various display modes are, of course, merely examples and owing to the presence of the signals representative of both the IR and visible images, any desired display mode may be designed, as is well known to those versed in the art. Thus, for example, it is possible to display on the monitor the infra-red image superimposed on the corresponding visible range image. Such a combined display (known also as video fusion) enables the surgeon to view both the visible surface of the object and, at the same time, the corresponding non-visible infra-red constituent, e.g. the carclio-vascular system.

In one practical embodiment, the image processes employed in the system in accordance with the present invention were IP-8; IMAGE-LC and MARVEL manufactured by Matrox Electronic Systems.

The system as described may serve in various applications. Thus, for example, in coronary vascular surgery it is possible to determine and decide where and how many grafts or by-passes are needed. In view of the real time nature of the system the surgeon may observe an image of the suspected area and trace stenosis or occlusion sites in which the blood flow will naturally be very slow. It has been found that by virtue of the real time nature of the system an infra-red anglogram taken in real time frequently differs from that taken prior to surgery utilizing, for example, an X-ray-based technique. In such a case the surgeon can change the plan of surgery so as to relate to the situation revealed and to transplant the graft in accordance with the real time infra-red anglogram.

The image processor can also provide for a "slow frames" feature which would allow, for example, for the readily observable display of the flow or perfusion of the blood or cardioplegia. This is of significant importance since in some cases a limited quantity of cardioplegia fluid can flow or diffuse very rapidly and it would otherwise be necessary for the surgeon to inject additional cardioplegia so as to be able to trace the fluid flow. By utilizing the slow frame feature the surgeon can view the rate of cardioplegia flow very carefully at a rate which is readily observable. The slow frame feature is particularly useful also when opening the LIMA or the RIMA or the DIAGONALS where the blood flow can be very fast.

A further possibility provided by the image processor is for the operator to freeze the frame when desired and to obtain a hard copy thereof, thereby obtaining a permanent anglogram before, during and after the operative stage.

The image processor can be so designed as to provide, for example, a direct indication of fluid flow, rates of perfusion, temperature variations and absolute determination of temperature, based on shade. Furthermore, quantitative or qualitative comparison of images which have been recorded at different stages of the operation can be obtained.

The surgical applications are, in fact, vast owing m the flexibility of the system and enable the surgeon to assess readily whether the blood flows and in which direction, how the coronary tree looks (before perfusion begins), whether the blood flows to the expected area, whether and where there are occlusions or stenosis which were not detected by the X-ray angiogram. The use of the system, for example in transplant operations, is readily indicated.

In addition to the surgical applications, the system can be used in various other medical applications wherein non-invasive examination of blood vessels is relevant including, as a diagnostic aid, for example in cases of skin cancer wherein the cancerous region is characterized by an abnormal profusion of blood vessels. Another instance is in the detection of circulatory problems where the rate and degree of blood flow and perfusion can be tracked in any desired area of the body. Thus, it is clear that the system can be used as a diagnostic aid as well.

Thus, for example, the image processor can be employed, upon receipt of a suitable command from the keyboard, to calculate the rate of blood flow in a graft. Thus, it will be realized that the quality and effectiveness of a surgical graft is directly related to the blood flow rate in the graft and a determination of this rate after grafting gives an indication of the success or otherwise of the operation. For this purpose, the appropriate function is entered into the keyboard (thereby providing the appropriate instruction to the image processor) and the surgeon manoeuvers the camera head until the display shows that the delineated portion thereof, corresponding to the location of the infra-red image, surrounds the grafted region under consideration. The blood flow in the graft is then interrupted (by suitable clamping) and the surgeon then injects into the graft a relatively cold saline solution which, in view of its relatively low temperature, will appear as black on the infra-red image display, whereas the surrounding relatively warmer regions will appear as grey or white. Upon unclamping of the graft, the cold saline solution will flow therethrough and the movement of this solution, and especially the tail portion thereof, can be tracked by the image processor. It will be readily understood bow, in this way, the flow rate of the cold saline solution in the graft can be determined by sampling, over predetermined time intervals, the position of the tail portion of the solution and its displacement within that time interval. Furthermore, and in order to have a more accurate determination, the procedure can be repeated and the flow rate can be calculated as the average of a plurality of measurements taken repetitively. The flow rate value so derived, together with predetermined data stored in a database, can be readily employed to provide information concerning the nature and degree of success of the grafting operation.

Where the nature of the graft is such that it is not possible to inject a cold saline solution (for example, in the case of arema or lima type grafts), flow rate can be determined on the basis of the degree of heat exchange. Thus, for this purpose the graft under consideration can be covered with a cold saline solution and, initially, the infra-red image displayed will show this region as relatively black. The rate of blood flow through the graft will be proportional to the rate of heat exchange between the warm blood and the surrounding cold saline solution, with a rapid blood flow rate resulting in rapid heat exchange and a relatively low blood flow rate resulting in a slower heat exchange. Thus, by measuring the time taken for the infra-red image display to change from substantially black to substantially white, the flow rate can be determined.

Similarly, it is possible to determine the quality of blood perfusion which is directly dependant on the blood flow rate into an area of interest such as, for example, a heart muscle. This can be done by measuring, for given time intervals, the grey level variation of the pixels located in the area of interest.

We claim:

1. An infra-red vascular angiography system comprising a readily displaceable camera including infra-red and visible range optical assemblies and infra-red and visible range detectors; the infra-red optical assembly being of high sensitivity for receiving and transmitting with minimal distortion an infra-red image of an object within an angular range of substantially ±45° with respect to a line perpendicular to the object; the infra-red range detector detecting the infra-red image transmitted from said optical assembly, in an infra-red wavelength range substantially between 8 to 12 micrometers, and converting it into a first set of successive electric output signals; a first video imaging device coupled to said infra-red range detector for digitizing said first set of output signals and converting them into a first set of successive digitized video image frames or successive portions thereof; the visible range optical assembly receiving and transmitting a visible image in coordination with said infra-red optical assembly and having a field of view with respect to said object which covers at least that of said infra-red assembly; the visible range detector converting the transmitted visible image into a second set of successive electric output signals; a second video imaging device coupled to said visible range detector for digitizing said second set of successive electric output signals into a second set of successive digitized video image frames or successive portions thereof; an image processor coupled to said first and second imaging devices adapted to receive said first and second successive video frames or successive portions of video frames to process them and form first and second sets of enhanced video images; and a switching device coupled to said image processor, for routing either or both of said sets of enhanced video images to a display device coupled to said image processor, for enabling an operator to readily correlate the infra-red image with the visible image of said object.

2. A system according to claim 1, and furthermore provided with a displacing handle fitted to said camera, said switching device being carried by said handle and being actuatable for switching purposes upon sensing of a contact or absence of contact with said handle.

3. A system according to claim 2, wherein said switching device is in the form of a micro-switch.

4. A system according to claim 2, wherein said switching device is an optical switch.

5. A system according to claims 1 or 2, wherein said visible range detector, said second video imaging device and at least a portion of said visible range optical assembly are included in a video camera.

6. A system according to claim 5, wherein said video camera is a CCD camera.

7. A system according to claim 1, wherein said switching device is keyboard operated.

8. A system according to claim 1, wherein said switching device is vocally operated.

9. A system according to claim 1, wherein said optical assemblies are each provided with an auto-focussing assembly.

10. A system according to claim 9, wherein the automatic focussing assembly of the infra-red optical assembly is enslaved to the automatic focussing assembly of the visible range optical assembly.

11. A system according to claim 1, wherein said display device displays said sets of enhanced video images respectively as thermal and visible range display zones with said thermal range display zone being wholly located within the visible range display zone.

12. A system according to claim 11, wherein said thermal range display zone is delineated within the visible range display zone by markings.

13. A system according to claim 11, wherein said thermal range display zone and said visible range display zone maintain a substantially constant spatial relationship with respect to each other independent of a location of the camera.

14. A system according to claim 13, wherein the thermal range display zone and the visible range display zone have a common center.

15. A system according to claim 1, wherein said optical assemblies have optical components in common.

16. A system according to claim 15, wherein a beam splitter assembly is included among said optical components and is adapted to receive radiation comprising infra-red and visible range constituents; the beam splitter being adapted to separate said received radiation into an infra-red constituent directed to the infra-red assembly, and a visible range constituent directed to the visible range assembly.

17. A system according to claim 1, further comprising a filter for filtering out radiation wavelength ranges other than predetermined visible and infra-red wavelength ranges.

18. A system according to claim 1 wherein the infra-red optical assembly comprises an infra-red lens which is adapted to be spaced from the object in a range of substantially 0.30 m to 100 m and wherein there is furthermore provided a first auto-focussing assembly for enhancing the infra-red image transmitted to said infra-red range detector.

19. A system according to claim 18, wherein said visible range optical assembly furthermore comprises a second auto-focussing assembly.

20. A system according to claim 19, wherein said first auto-focussing assembly is enslaved to the second.

21. A system according to claim 1 and furthermore comprising an auxiliary portable probe for viewing and transmitting an infra-red image of a region of said object closely adjacent said probe and comprising a housing; at least a further infra-red lens forming a window in said housing and adapted to be juxtaposed with respect to said region; an optical fiber assembly having a first end portion located within said housing remote from said window and having a second and opposite end portion juxtaposed with respect to said infra-red range detector; and an optical system located in said housing and adapted to project an infra-red image transmitted by said window onto said first end portion of said optical fiber assembly.

22. A system according to claim 21, wherein said auxiliary portable probe is in the form of an elongated, substantially cylindrical probe comprising a tubular housing having at its front end an infra-red window.

23. A system according to claim 21, wherein said auxiliary portable probe further comprises a lens system which serves for focussing of the image onto a bundle of optical fibers protruding from the housing.

24. A system according to claim 23, wherein the opposite end portion of the bundle is secured to a coupling unit which is provided with means facilitating readily and releasably coupling to an appropriate location in a camera housing.

25. A system according to claim 21, wherein said infra-red image has a plurality of picture elements transmitted, each, via a distinct fiber of said bundle.

26. A system according to claim 21, wherein the auxiliary probe is provided with several infra-red windows enabling a surgeon to view images from various directions.

27. A system according to claim 23, wherein the probe is provided with a scanner assembly so as to facilitate a projection of discrete image signals onto a relatively limited number of optical fibers, thereby reducing a size of the bundle of optical fibers.

28. A system according to claim 21, wherein the probe is further provided with an automatic focussing mechanism.

29. A system according to claim 1, wherein said defective cell compensator incorporates art Extending Soble Filter technique.

30. A system according to claim 1, and furthermore comprising a defective cell compensator for assigning a compensated value to at least one picture element originating from a defective cell included in said infra-red range detector; the compensated value being determined on a basis of at least one picture element value originating from a non defective cell in the proximity of the defective cell.

31. A system according to claim 30, wherein said defective cell compensator incorporates a bi-linear transformation technique.

32. A system according to claim 1, wherein said infra-red optical assembly includes a lens of 500 mm focal length and made on either ZnS or Ge.

33. A system according to claim 1, wherein said infra-red detector means comprises a linear or bi-dimensional detector array of infra-red cells.

34. A system according to claim 33, wherein each individual detector cell is made of MCT alloy.

35. A system according to claim 1, and furthermore comprising a console member and a readily displaceable camera assembly member; said camera assembly member including at least said infra-red and visible range optical assemblies and infra-red range detector; and wherein said console member includes at least said image processor; and said first and second video imaging devices and a cooling unit, adapted to continuously maintain the infra-red range detector at an essentially fixed temperature, located in one or other of said member; the system further including a mechanical coupler for coupling said console member to said camera assembly member and an electrical and/or optical coupler for coupling together constituent components in said member.

36. A system according to claim 35, wherein the console and the camera assembly are fitted each with means for transportation and are mechanically coupled to each other in the form of a detachable coupling whereby the camera assembly is transportable independent of said console.

37. A system according to claim 35, wherein said cooling unit is a closed loop cooling unit located in said camera assembly.

38. A system according to claim 1, and furthermore comprising a video recorder adapted to receive and record said first and second sets of enhanced video frames.

39. An infra-red vascular angiography system comprising a readily displaceable infra-red camera comprising a camera housing and including an infra-red optical assembly of high sensitivity for receiving and transmitting with minimal distortion an infra-red image of an object within an angular range of substantially ±45° with respect to a normal to the object; an infra-red range detector for detecting the infra-red image transmitted from said optical assembly, in an infra-red wavelength range substantially between 8 to 12 micrometers, and converting it into successive electric output signals; a video imaging device coupled to said infra-red range detector for digitizing said output signals and converting them into successive digitized video image flames or successive portions thereof; an image processor coupled to said imaging device for receiving the successive video frames or successive portions of video frames to process them and form enhanced video images and a display device coupled to said image processor;

the system further comprising an auxiliary portable probe for viewing and transmitting an infra-red image of a region of said object closely adjacent said probe wherein said probe comprises a housing; at least a further infra-red lens forming a window in said housing and adapted to be juxtaposed with respect to said region; an optical fiber assembly having a first end portion located within said housing remote from said window and having a second and opposite end portion juxtaposed with respect to said infra-red range detector; and an optical system located in said housing and adapted to project an infra-red image transmitted by said window onto said first end portion of said optical fiber assembly.

40. A system according to claim 39, wherein said auxiliary portable probe is in the form of an elongated, substantially cylindrical probe comprising a tubular housing having at its front end an infra-red window.

41. A system according to claim 39, wherein said auxiliary portable probe further comprises a lens system which serves for focussing of the image onto a bundle of optical fibers protruding from the housing.

42. A system according to claim 41, wherein the probe is provided with a scanner assembly for projecting discrete image signals onto a relatively limited number of optical fibers, thereby reducing a size of the bundle of optical fibers.

43. A system according to claim 41, wherein the opposite end portion of the bundle is secured to a coupling unit which is provided with means for readily and releasably coupling the bundle to an appropriate location in said camera housing.

44. A system according to claim 39, wherein said infra-red image has a plurality of picture elements transmitted, each, via a distinct fiber of said bundle.

45. A system according to claim 39, wherein the auxiliary probe is provided with several infra-red windows enabling a surgeon to view images from various directions.

46. A system according to claim 39, wherein the probe is further provided with an automatic focussing mechanism.

47. An infra-red vascular angiography system comprising a readily displaceable infra-red camera including an infra-red optical assembly of high sensitivity for receiving and transmitting with minimal distortion an infra-red image of an object within an angular range of substantially ±45° with respect to a normal to the object; an infra-red range detector for detecting the infra-red image transmitted from said optical assembly, in an infra-red wavelength range substantially between 8 to 12 micrometers, and converting it into successive electric output signals; video imaging device coupled to said infra-red range detector for digitizing said output signals and converting them into successive digitized video image frames or successive portions thereof; an image processor coupled to said imaging device for receiving the successive video frames or successive portions of video frames to process them and form enhanced video images and a display device coupled to said image processor;

the infra-red optical assembly comprising an infra-red lens which is adapted to be spaced from the object in a range of substantially 0.30 m to 1.00 m and wherein there is furthermore provided an automatic focussing assembly for enhancing the infra-red image transmitted to said infra-red range detector.

48. An infra-red vascular angiography system comprising a readily displaceable infra-red camera including an infra-red optical assembly of high sensitivity for receiving and transmitting with minimal distortion an infra-red image of an object within an angular range of substantially ±45° with respect to a normal to the object; an infra-red range detector for detecting the infra-red image transmitted from said optical assembly, in an infra-red wavelength range substantially between 8 to 12 micrometers, and converting it into successive electric output signals; a video imaging device coupled to said infra-red range detector for digitizing said output signals and converting them into successive digitized video image frames or successive portions thereof; art image processor coupled to said imaging device adapting to receive the successive video frames or successive portions of video frames to process them and form enhanced video images and a display device coupled to said image processor;

said image processor incorporating a defective cell compensator for assigning a compensated value to at least one picture element originating from a defective cell included in said infra-red range detector; said compensated value being determined on a basis of at least one picture element value originating from a non defective cell located in proximity to the defective cell.

49. A system according to claim 48, wherein said defective cell compensator means operates on the basis of the Extending Soble Filter technique.

50. A system according to claim 48, said defective cell compensator means incorporating the bi-linear transformation technique.

51. An infra-red vascular angiography system comprising a readily displaceable infra-red camera including an infra-red optical assembly of high sensitivity for receiving and transmitting with minimal distortion an infra-red image of an object within an angular range of substantially ±45° with respect to a normal to the object; an infra-red range detector for detecting the infra-red image transmitted from said optical assembly, in an infra-red wavelength range substantially between 8 to 12 micrometers, and converting it into successive electric output signals; a video imaging device coupled to said infra-red range detector for digitizing said output signals and converting them into successive digitized video image frames or successive portions thereof; an image processor coupled to said imaging device for receiving the successive video frames or successive portions of video frames to process them and form enhanced video images and a display device coupled to said image processor;

and furthermore comprising a console member and a readily displaceable camera assembly member; said camera assembly member including at least said infra-red range assembly and infra-red range detector; and wherein said console member includes at least said image processor; and said video imaging device and a cooling unit, adapted to continuously maintain the infra-red range detector at an essentially fixed temperature, located in one of said members; the system further including a mechanical coupler for coupling said console member to said camera assembly member and an electrical and/or optical coupler for coupling together constituent components in said member.

52. A system according to claim 51 wherein said cooling unit is a closed loop cooling unit located in said camera assembly.

53. A system according to claim 52, wherein the console members and the camera assembly member are fitted each with means for transportation and are mechanically coupled to each other by a detachable coupling wherein the camera assembly member is transportable independent of said console member.

* * * * *